(12) United States Patent
Au et al.

(10) Patent No.: US 8,802,138 B2
(45) Date of Patent: Aug. 12, 2014

(54) METHODS AND COMPOSITIONS FOR IMPROVED DELIVER, EXPRESSION OR ACTIVITY OF RNA INTERFERENCE AGENTS

(76) Inventors: Jessie L.-S. Au, San Diego, CA (US); M. Guillaume Wientjes, San Diego, CA (US); Ze Lu, Upper Arlington, OH (US); Jie Wang, Columbus, OH (US)

(*) Notice: Subject to any disclaimer, the term of this patent is extended or adjusted under 35 U.S.C. 154(b) by 0 days.

(21) Appl. No.: 13/444,798

(22) Filed: Apr. 11, 2012

(65) Prior Publication Data

US 2012/0225115 A1    Sep. 6, 2012

Related U.S. Application Data

(63) Continuation-in-part of application No. 12/719,546, filed on Mar. 8, 2010, now abandoned.

(60) Provisional application No. 61/250,587, filed on Oct. 12, 2009.

(51) Int. Cl.
| | | |
|---|---|---|
| A61K 9/127 | (2006.01) | |
| A61K 31/7105 | (2006.01) | |
| A61K 31/713 | (2006.01) | |
| C12N 5/09 | (2010.01) | |
| A61P 35/00 | (2006.01) | |
| A61K 31/704 | (2006.01) | |

(52) U.S. Cl.
USPC ............ 424/450; 514/44 A; 514/34; 435/375

(58) Field of Classification Search
USPC .......................................................... 424/450
See application file for complete search history.

(56) References Cited

U.S. PATENT DOCUMENTS

| | | | | |
|---|---|---|---|---|
| 2008/0033156 A1* | 2/2008 | Vargeese et al. | ............. | 536/23.1 |
| 2008/0312096 A1* | 12/2008 | Gray et al. | ........................ | 506/9 |
| 2009/0239818 A1* | 9/2009 | Cheng | ............................. | 514/52 |

FOREIGN PATENT DOCUMENTS

WO    WO-2009-142892    * 11/2009

OTHER PUBLICATIONS http://www.accessdata.fda.goy/drugsatfda_docs/label/2012/021660s031lbl.pdf.*

* cited by examiner

*Primary Examiner* — Frederick Krass
*Assistant Examiner* — Celeste A Roney
(74) *Attorney, Agent, or Firm* — Mueller Law, LLC; Jerry K. Mueller, Jr.

(57) ABSTRACT

The present disclosure provides methods and compositions for enhanced delivery of siRNA or miRNA, into the interior of multilayered tissues, and into the cytoplasm or nucleus of cells of a tissue. Such methods and compositions yield tumor-selective and intracellular delivery of RNAi agents and allow for RNAi-mediated activity such as knock-down of the target genes and associated products. The current disclosure further provides methods and compositions for improving the intracellular bioavailability of nucleotide agents.

20 Claims, 7 Drawing Sheets

METHODS AND COMPOSITIONS FOR IMPROVED DELIVER, EXPRESSION OR ACTIVITY OF RNA INTERFERENCE AGENTS

CROSS-REFERENCE TO RELATED APPLICATIONS

This application claims benefit of Provisional Application No. 61/250,587, entitled "Methods and compositions for improved management and treatment of patients with tumors or proliferative disorders", filed on Oct. 12, 2009; is a continuation-in-part of application Ser. No. 12/719,546, filed on Mar. 8, 2010, and entitled, "Methods and Compositions for Improved Delivery, Expression or Activity of RNA Interference Agents"; which was a confirmation of application serial number PCT/US10/52326, filed on Oct. 12, 2010, entitled, "Methods and Compositions for Improved Delivery, Expression or Activity of RNA Interference Agents". The entire content of these applications are hereby incorporated herein by reference. The contents of all patents, patent applications, and references cited throughout this application are hereby incorporated by reference in their entireties.

STATEMENT REGARDING FEDERALLY SPONSORED RESEARCH

This work was supported, in part, by a research grant from the United States Department of Health and Human Services (Grant number R43CA134047).

OVERVIEW

RNA interference (RNAi) can be used to correct genetic aberrations. A major impediment to the successful use of RNAi is the inability to deliver RNAi agents to cells or to cause expression of RNAi in cells. This is particularly problematic for abnormal growths that do not have good blood perfusion. The present disclosure provides methods and compositions for delivering or enhancing the intracellular bioavailability of RNAi agents.

BACKGROUND

Gene Therapy: Difference Between DNA- and RNA-Directed Gene Therapy

The concept of gene therapy, or correcting the disease-causing faulty genes, was introduced several decades ago. The initial attempt was to use DNA-directed gene therapy where the DNA therapeutics and their carriers have to enter the nucleus to exert actions.

A newer form of gene therapy directed at RNAs, RNA interference (RNAi), was introduced in the last decade. RNAi therapeutics are short stretch double-stranded RNA that degrade the complementary mRNA, and thereby produce sequence-specific post-transcriptional gene silencing and correct the expression of faulty genes or production of disease-causing proteins. The RNAi process occurs in the cytoplasm. The two types of RNAi are small interfering RNA (siRNA) and microRNA (miRNA). Both use the same enzymes and proteins to produce gene silencing. A siRNA targets a single mRNA whereas miRNA may target 250-500 different mRNAs.

There are several major differences between DNA- and RNA-directed gene therapy. First, the formulations of DNA and RNAi vectors are different. For example, relatively large DNA lipoplexes (e.g., with a diameter ranging from 0.4 to 1.4 micron) show more efficient transfection in cultured cells compared to smaller lipoplexes. In contrast, RNAi vectors such as those disclosed in the instant disclosure are smaller in size, e.g., in the nanometer range. Second, for DNA-directed gene therapy, the DNA therapeutics must travel across the cell membrane and the cytosol to reach the nucleus, which involves the following multiple processes: (a) Binding of vectors to the cell. (b) Internalization of DNA therapeutics through endocytosis and endosome formation. (c) After internalization, the DNA-vector complexes (lipoplexes or polyplexes) are released from endosomes. (d) Cytoplasmic transport of endosomes may bring the complexes near the perinuclear region in such a way that the released DNA would have a greater chance to enter the nucleus. (e) Dissociation of lipoplexes, resulting in separation of DNA and vector. (f) Lipoplexes or polyplexes that are unable to escape from endosomes are likely to be degraded in lysosomes. (g) DNA released from lipoplexes or polyplexes into the cytoplasm may enter the nucleus via different, non-mutually exclusive, mechanisms. One, DNA may enter the nucleus during mitosis when the nuclear membrane breaks down. The second mechanism involves an active, energy-dependent nuclear transport into the nucleus. This transport requires the presence of specific sequences in the plasmid that mediate its interaction with transport proteins such as importins and other nuclear transport mediators. Three, lipoplex-filled endosomes may fuse directly with the nuclear membrane, permitting a direct entry of DNA into the nucleus. (h) After entering the nucleus, the DNA-therapeutic is degraded or integrated into the host chromatin.

In contrast, RNAi therapeutics exert their actions in the cytosol and do not require entering the nucleus or interaction with chromosomal DNA. However, the other barriers up to the step of being released as intact RNAi agent in the cytosol remain.

Due to the above differences, the efficiency of DNA- and RNA-directed gene therapy has different requirements. Increase of the transfection of DNA-therapeutics can occur at any one of the eight steps involved in a successful DNA gene therapy outlined above. In contrast, RNAi transfection can be increased by improving the delivery (including being released from the vector and endosomes) of RNAi to, and its expression in, the cytosol. These differences are substantive. For example, early release of DNA complex from endosomes is undesirable as the released DNA is subjected to degradation by cytoplasmic nucleases. In contrast, early release of RNAi from endosomes to the cytosol is desired as the released RNAi can then induce gene silencing. Similarly, pen-nuclear accumulation of DNA complex is desired for enhancing the DNA entry into the nucleus. In contrast, pen-nuclear accumulation is not necessary for RNAi. In other words, approaches and delivery systems that work in DNA-directed gene therapy may not be applicable to RNA-directed gene therapy, and vice versa.

Statement of Problems

While RNAi is useful to study research problems in experimental systems such as cultured cells, it is well recognized that the single most important impediment to the successful utilization of RNAi therapy in vivo in a patient or an animal is the difficulty in achieving adequate delivery or transfection of RNAi agents to the diseased cells or the cytosol of the diseased cells where the siRNA or miRNA molecules exert their actions. This limitation on the use of RNA interference therapy is so severe that recently, Sirna Therapeutics Inc., a wholly owned subsidiary of Merck & Co. Inc., publicly asked the research community for help in identifying methods and compositions to overcome this limitation (Sirna Therapeutics Inc, Http://Www.Sirna.Com, 2009). The barriers and the carriers for RNAi are discussed in a recent review (Wang, *AAPS. J.*, 2010).

PRESENT DISCLOSURE

Brief Summary

This application discloses methods and compositions of RNAi vectors that are effective in delivering RNAi agents and achieving RNA interference in vitro and in vivo. The disclosure is based on Applicants' finding that certain drugs, referred to as enabler agents, improve the delivery of RNAi vectors or RNAi agents to tumor cells and enhance the release of RNAi agents from carriers, endosomes or lysosomes in the cytosol, and thereby enhance the intracellular bioavailability of RNAi agents. The ability of RNAi to reach the cellular RNA interference machinery is required for effective RNA interference treatment. The enabler agent is one or more of tubulin-active agents, including, inter alia, paclitaxel, docetaxel, colchicine, nocodazole and vincristine, and topoisomerase inhibitors including, inter alia, doxorubicin. Other drugs that do not have tubulin- or topoisomerase-directed actions cannot enhance the intracellular bioavailability of RNAi agents.

The compositions comprise combinations of one or more of enabler agents with RNAi vectors. The combinations are termed RNAi delivery and expression system (RIDES), comprising two components. One component is the newly disclosed PEGylated cationic liposomal RNAi vector, comprising DOTAP and cholesterol plus a neutral phospholipid DOPE with a PEGylated lipid DSPE-PEG2000, in a molar ratio of 50:30:19:1. This vector, referred to as PCat liposomes, has not been described in the art. Applicants have shown in side-by-side comparisons, outlined in Examples 4-6, that this PCat vector is more effective in delivering and expressing RNAi and produces less toxicity under in vitro and in vivo situations, compared to the cationic liposome formulation of 50:50 DOTAP:Cholesterol well-known in the art (U.S. Pat. No. 5,459,127). The second component of RIDES is one or more of enabler agents. The two components of RIDES can be given in several ways. One way is to prepare the two components in separate formulations and administer both concurrently. Another way is to give the enabler agent, e.g., a few hours to a few days, before the RNAi agent. The third way is to put both agents in the same PCat vector, and administer the resulting preparation as a single entity.

The methods include using one or more of enabler agents to improve the delivery of RNAi to tumor cells and to enhance the intracellular bioavailability of RNAi in the cytosol such that the combinations produce greater benefits in cultured cells or in vivo, i.e., in a human patient or an animal, relative to without the use of enabler agent. Use of RIDES can be effectively applied to positively charged liposomes and to liposomes that are pegylated.

Additional compositions and methods are combinations of apoptosis-inducing agents with RIDES. The apoptosis-inducing agent is prepared as rapid-release or slow-release formulations or the clinically used formulation.

As disclosed in the examples, Applicants have successfully formulated RNAi agents in the PCat liposomes, and shown effective delivery of RNAi to cells and release of RNAi from carriers, endosomes or lysosomes in the cytosol, resulting in effective RNA interference and suppression of protein synthesis in cultured cells and in vivo in tumor-bearing animals.

As siRNA and miRNA have similar chemical structures (both are dsRNA oligonucleotides of lengths of approximately 21-27 nucleotide units) and act on the same mRNA destruction machinery in the cytosol, the same delivery systems can be used for both types of RNAi.

BROAD STATEMENT

This disclosure provides methods and compositions for delivering RNAi agents to their site of action in the cytosol of a cell where they are able to produce RNA interference.

BRIEF DESCRIPTION OF THE DRAWINGS

For a fuller understanding of the nature and advantages of the present process and compositions, reference is made to the following detailed description taken in connection with the accompanying drawings, in which:

The methods are described in Example 2. FIG. 1A shows the representative animals on day 21. FIG. 1B shows the photomicrographs of tumor sections stained for total survivin, nuclear survivin, caspase 3 (marker for apoptosis) and Ki67 (marker for proliferating cells).

Mice bearing human xenograft tumors were treated as described in Example 3. Paclitaxel was dissolved in Vehicle (i.e., 50:50 v/v Cremophor®:ethanol). Photographs of representative animals are shown. Some animals showed small or no residual tumors (arrows indicate the site of tumor implantation). Panel A: animals bearing pancreatic Hs766T tumors, at day 10 after initiation of treatment. Panel B: animals bearing prostate PC3 tumors, at day 21 after initiation of treatment. Panel C: animals bearing pharynx FaDu tumors, at day 42 after initiation of treatment. In Panel C, no animals in the three groups receiving Vehicle are shown because all had reached moribundity before day 42. N/A, not available.

Figure 3:
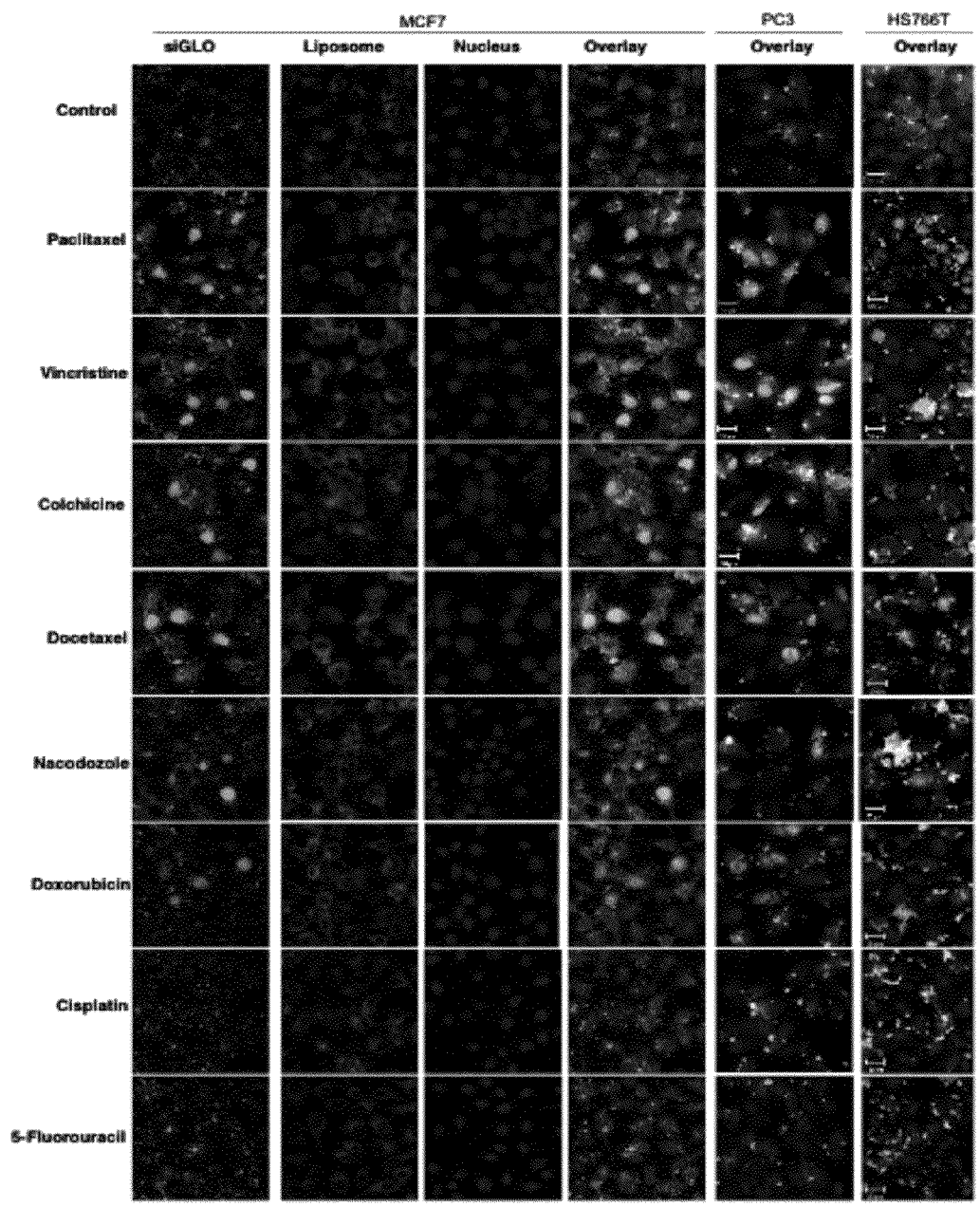

FIG. 3. Pretreatment with enabler agents improves the intracellular bioavailability of RNAi.

The methods are described in Example 7. Monolayer cultures of human breast tumor MCF7, prostate PC3, and pancreatic Hs766T were pretreated with an enabler agent and then with DC-RNAi. The control group was not treated with enabler agent. The RNAi was siGLO. The nuclei were labeled with DRAQ5 (blue fluorescence). siGLO shows green fluorescence. Lipids show red fluorescence. Co-localization of punctuated red and green signals (which yields a mixed color ranging from yellow to green) indicates the intact siRNA loaded in liposomes. Co-localization of green and blue signals (which yields a mixed color ranging from turquoise to green) indicates the presence of siGLO in the nucleus. Slight variations in the mixed colors are due to experimental variability. In some cells, green signal is diffusely spread throughout the nucleus indicating extensive dissociation of siGLO from the liposomes and effective transfection. Both events were enhanced by the enabler agent. This indicates the enabler agent promoted the release of RNAi from carriers, endosomes or lysosomes, or improved the RNAi delivery to the cytosol and nucleus. Other chemotherapeutic agents that are not tubulin-active or topoisomerase-inhibitory, i.e., cisplatin or 5-fluorouracil, were found in side-by-side comparison to be ineffective. Bar, 20 μm.

Figure 4:
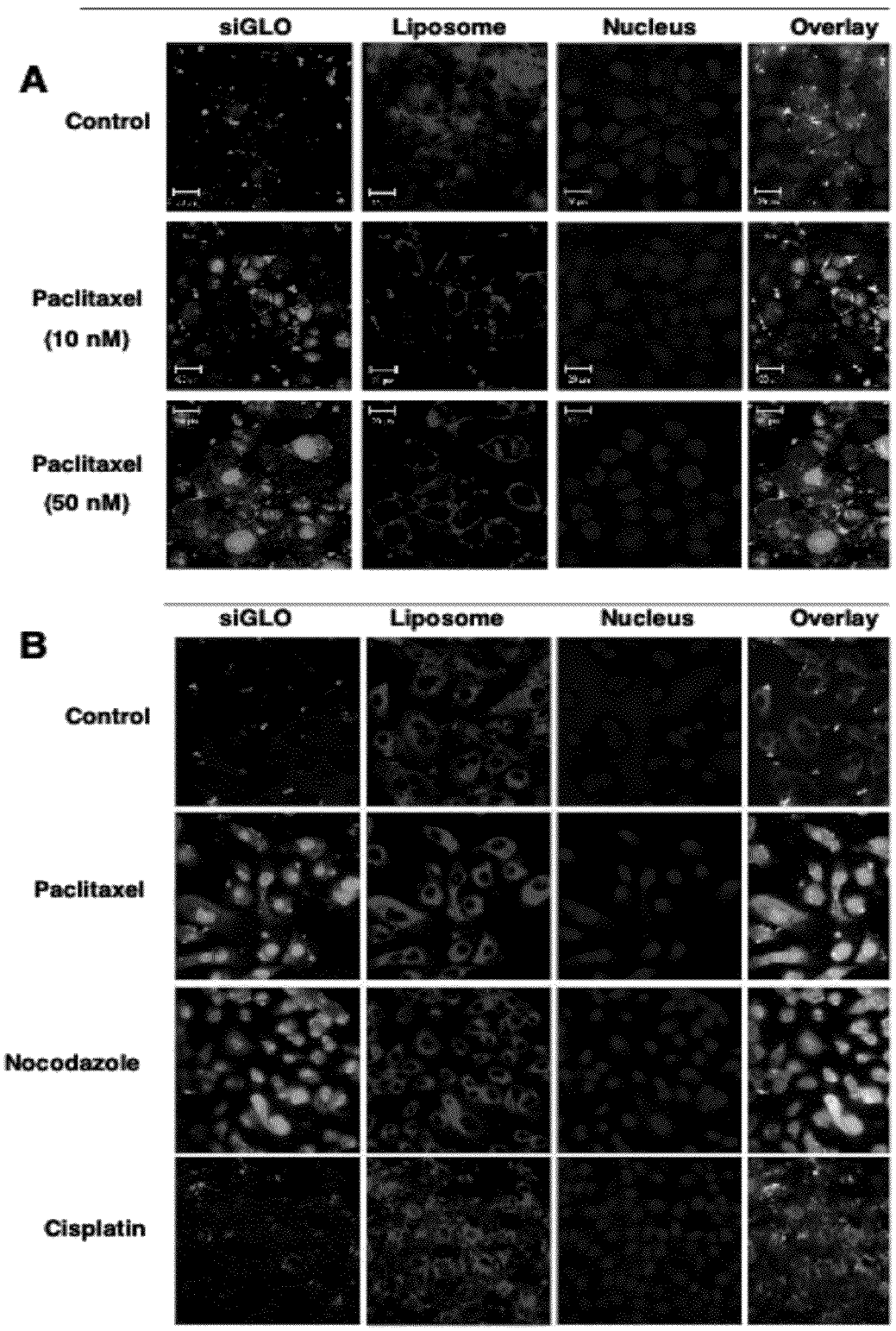

FIG. 4. Enabler agents, under diverse conditions, enhance intracellular bioavailability of RNAi.

The confocal microscopy results are shown. Bar, 20 μm. Panel A: The enabler agent paclitaxel is effective when given at cytotoxic concentration (50 nM) or non-cytotoxic (10 nM) concentration. The methods are described in Example 7, second study. Panel B: The enabler agents are effective when administered simultaneously with PCat-RNAi (in separate solutions). The methods are described in Example 7, third study. A chemotherapeutic agent that is not tubulin-active or topoisomerase-inhibitory (cisplatin), was found in a side-by-side comparison to be ineffective in promoting the delivery or release of RNAi from liposomes, endosomes or lysosomes. These results indicate the enabler agents improve the delivery and release of RNAi from liposomes, endosomes, and lysosomes.

Figure 5:
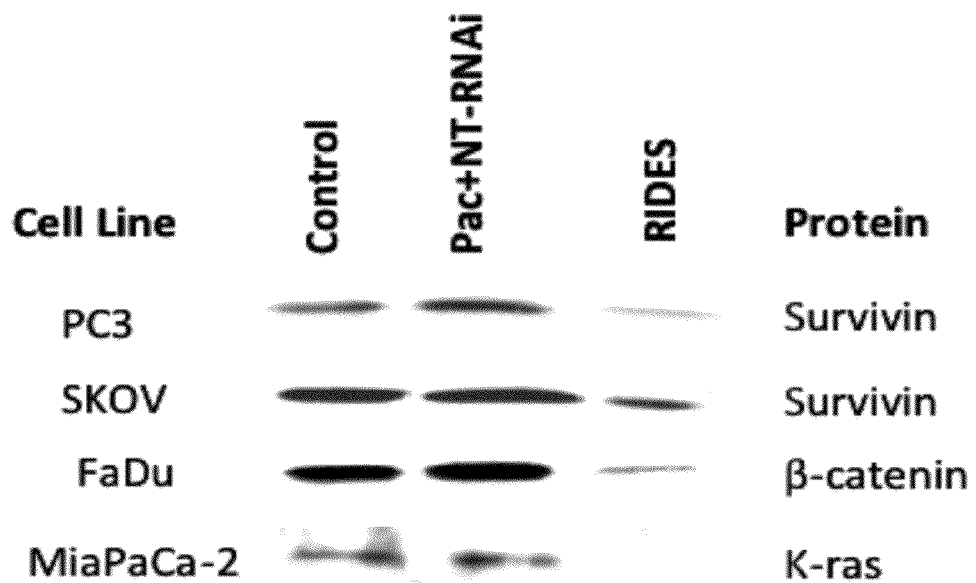

FIG. 5. RIDES is effective in producing knockdown of target proteins. The effectiveness of RNAi was measured by the reduction of the level of the targeted protein using western blotting. The methods are described in Example 10.

Figure 6:
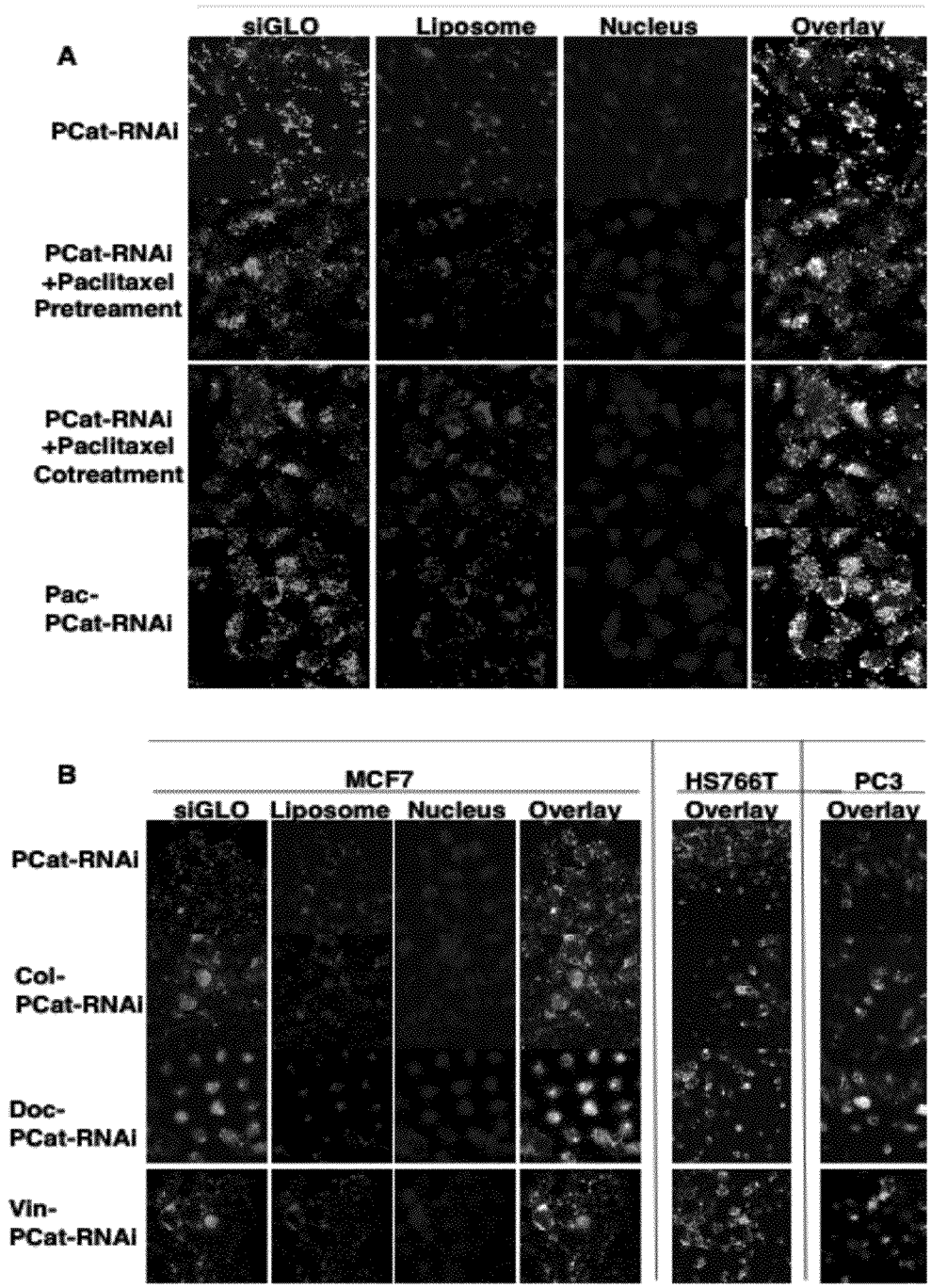

FIG. 6. Effects of different ways of combining the two components of RIDES on the intracellular bioavailability of RNAi.

Panel A: The methods are described in Example 11. Monolayer cultured PC3 cells were used. The RNAi was siGLO. Confocal fluorescence microscopy was used to visualize the location of siGLO (green), lipids (red), and nucleus (blue). The two components of RIDES, i.e., enabler agent and PCat-RNAi, were administered in three different ways. The enabler agent was paclitaxel. One composition of RIDES was to administer the enabler agent before PCat-RNAi (i.e., PCat-RNAi+paclitaxel pretreatment). The second composition was to administer the enabler agent concurrently with PCat-RNAi (i.e., PCat-RNAi+paclitaxel cotreatment). In these two cases, the two RIDES components were administered in separate preparations. The third composition was as a single entity where both agents were loaded in PCat liposomes (i.e., Pac-PCat-RNAi). Panel B: Three additional enabler agents loaded together with RNAi in PCat liposomes, i.e., docetaxel, colchicine, and vincristine; the corresponding composition was Doc-PCat-RNAi, Col-PCat-RNAi, and Vin-PCat-RNAi. The study was performed in PC3, MCF, and Hs766T cells. The enhanced presence of siGLO in the nucleus indicates the enabler agents promoted the delivery and release of RNAi from liposomes, endosomes, and lysosomes. Bar, 20 μm.

Figure 7:
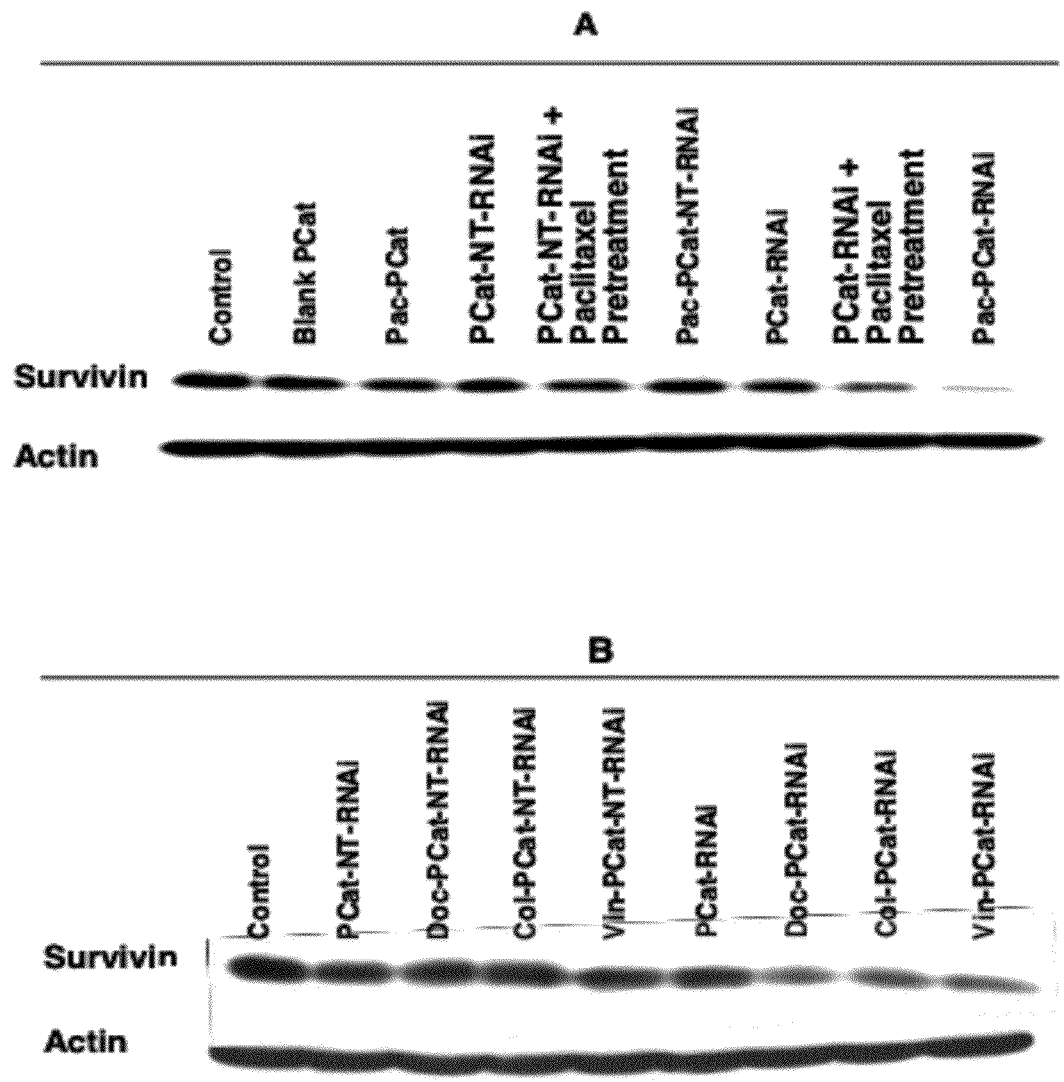

FIG. 7. Enabler-containing PCat-RNAi is effective in producing RNA interference.

The study used PCat liposomes containing both enabler agent and RNAi. The enabler agents were paclitaxel, docetaxel, colchicine, or vincristine, and the corresponding PCat-RNAi were Pac-PCat-RNAi, Doc-PCat-RNAi, Col-PCat-RNAi, and Vin-PCat-RNAi. The RNAi agent was the survivin siRNA. The methods are as described in Example 12. The western blot results are shown. Panel A: Comparison of enabler-containing PCat-RNAi to the separate administration of enabler agent (given as pretreatment) and PCat-RNAi. Paclitaxel was used as the enabler agent. Panel B: Effectiveness of Doc-PCat-RNAi, Col-PCat-RNAi, and Vin-PCat-RNAi.

DETAILED DESCRIPTION

This disclosure provides methods and compositions for delivering RNAi agents to cells and for enhancing the intracellular bioavailability of RNAi agents, both in vitro and in vivo.

Applicants have previously disclosed the use of the tumor-priming method to enhance delivery of therapeutic agents, as described in U.S. patent application Ser. No. 09/547,825, entitled "Methods and compositions for enhancing delivery of therapeutic agents to tissue", filed on Apr. 7, 2000, and in U.S. patent application Ser. No. 11/242,546 filed on Apr. 3, 2005 and entitled: "Tumor-Targeting Drug-Loaded Particles". These prior disclosures describe methods and compositions to use apoptosis-inducing agents to enhance delivery of therapeutic agents, but did not consider delivery of RNAi agents and did not disclose the newly discovered PCat liposomal RNAi carriers. As discussed throughout this document, the delivery of RNAi agent present special challenges to the field that can not be readily resolved with standard and generally available methods and compositions in the art. For these reasons, Applicants' previous disclosures do not anticipate the current methods or compositions.

1. DEFINITIONS

In order to provide a clear and consistent understanding of the disclosure, certain terms employed herein in the specification, examples, and the claims are, for convenience, collected here.

The terms "proliferative disorders" or "aberrant growth" refer to a cell phenotype, which differs from the normal phenotype of the cell, particularly those associated either directly or indirectly with a disease such as cancer.

The term "in vitro" refers to conditions that are not in a living organism but in a controlled environment.

The term "in vivo" refers to conditions that are in a living organism, e.g., inter alia, a mammal, a human, an animal, a plant.

The term "administering" refers to the introduction of an agent to a cell, e.g., in vitro, to a cell in a mammal, i.e., in vivo, or to a cell later placed back in a mammal (i.e., ex vivo).

The terms "enabler agent" or "enabler" are used interchangeably, and refer to an agent that can enhance the intracellular bioavailability of RNAi agents in vitro or in vivo, though enhancing the delivery of RNAi to a cell or promoting the release of RNAi from its carriers, endosomes, and lysosomes in the cytosol of a cell in culture or in vivo in a subject.

The term "RNA interference" or "RNAi" refers to the silencing or decreasing of gene expression by RNAi agents (e.g., "short interfering RNA", "siRNA", "shRNA", "short interfering nucleic acid molecule", "short interfering oligonucleotide molecule", or "chemically-modified short interfering nucleic acid molecule"). The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference (see, e.g., (Grimm, *Adv. Drug Deliv. Rev.*, 61, 672, 2009; Gondi, *J. Cell Physiol*, 220, 285, 2009; Carthew, 136, 642, 2009; Jinek, 457, 405, 2009; Ghildiyal, *Nat. Rev. Genet.*, 10, 94, 2009). RNAi is the process of sequence-specific, post-transcriptional gene silencing in cells, animals and plants, initiated by an RNAi agent that is homologous in its duplex region to the sequence of the to-be-silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be completely or partially inhibited.

In some embodiments, the RNAi agent can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The RNAi agent can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the RNAi agent is assembled from a single oligonucleotide, where the self-complementary sense and antisense regions of the RNAi agent are linked by means of a nucleic-acid-based or non-nucleic acid-based linker(s). The RNAi agent can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The RNAi agent can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active small nucleic acid molecule capable of mediating RNAi. The RNAi agent can also comprise a single stranded polynucleotide having nucleotide sequence complementary to nucleotide sequence in a target nucleic acid molecule or a portion thereof. For present purposes, RNAi agent molecules need not be limited to those molecules containing only naturally occurring RNA, but further encompasses chemically-modified nucleotides and non-nucleotides.

The term "RNAi agent" is meant to be equivalent to other terms used to describe nucleic acid molecules that are capable of mediating sequence specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics. As used herein, "siRNA" frequently refers to artificial nucleotide sequences that are used in RNA interference therapy. Typically, an siRNA is a double-stranded nucleic acid molecule comprising two nucleotide strands, each strand having about 19 to about 28 nucleotides.

A short hairpin RNA (shRNA) is a sequence of RNA that makes a tight hairpin turn that can be used to silence gene expression via RNA interference. It is typical to use a vector to introduce shRNA into cells and to use a promoter (e.g., the U6 promoter) to ensure that the shRNA is expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

MicroRNAs (miRNAs) are a class of endogenous, single or double-stranded, about 22 nucleotide-long RNA molecules that regulate as much as 30% of mammalian genes, with important roles in regulation of cellular differentiation, proliferation, and apoptosis. Specific patterns of up- and down-regulation of miRNAs in various human tumor types are recognized. miRNA represses protein production by blocking translation or causing transcript degradation.

The term "faulty gene" refers to a gene that is altered such that it causes a disorder.

The terms "gene knockdown", "knockdown", or "knockdown" are used interchangeably and refer to techniques by which the expression of one or more of an organism's genes is reduced, either through genetic modification (a change in the DNA of one of the organism's chromosomes) or by treatment with a reagent such as a short DNA or RNA oligonucleotide with a sequence complementary to either an mRNA transcript or a gene. Knockdown using RNAi agents changes gene expression through, inter alia, degradation of the mRNA, blocking of the mRNA translation, or blocking maturation of pre-mRNA to mRNA.

The terms "siRNA against (name of a gene)", "anti-(name of a gene) siRNA" are used interchangeably and refer to an siRNA that is directed at a gene for the purpose of silencing the gene.

The terms "expression" and "transfection" of the RNAi agents are used interchangeably, and refer to the activity of the RNAi agents after delivery inside the cell. A high expression or transfection indicates effective knockdown of the target protein or proteins. For siGLO, a green-fluorescent dsRNA molecule designed to be transported to the nucleus after delivery to the cytosol of a cell and after release from the vectors or endosomes as a free molecule, expression or transfection is indicated by the accumulation of green fluorescence in the nucleus of the cell.

The term "intracellular bioavailability of an RNAi agent" refers to the RNAi agent that is released intact, i.e., not degraded, from its carrier, endosomes or lysosomes, that is generally available for reaching the intracellular RNAi machinery, or that is functional in achieving its RNA interference action.

The term "RIDES" refers to a multi-component RNAi vector system that can be used for administration of RNAi agents. RIDES stands for RNAi delivery and expression system. One component of RIDES is a pegylated liposomal cationic RNAi vector, PCat liposomes. The other component of RIDES comprises one or more of paclitaxel, doxorubicin, other tubulin-active agents, or other topoisomerase inhibitors. The inclusion of one or more of these agents is to improve the delivery of RNAi vectors, including PCat-siRNA, to cells and to improve the release of RNAi from its carriers, endosomes, and lysosomes to the cytosol and the resulting gene silencing.

The terms "PCat liposomes" and "PCat" are used interchangeably, and refer to a pegylated liposomal cationic RNAi vector, comprising DOTAP and cholesterol plus a neutral phospholipid DOPE with a pegylated lipid DSPE-PEG2000, in a molar ratio of 50:30:19:1.

The term "PCat-RNAi" refers to PCat liposomes containing an RNAi agent.

The terms "enabler-loaded" and "enabler-containing" are used interchangeable. The term "enabler-loaded PCat-RNAi" refers PCat liposomes containing an RNAi agent and an enabler agent. The enabler agent can be one or more of tubulin-active agents, i.e., inter alia, paclitaxel, docetaxel, colchicine, nocodazole, vincristine, and cabazitaxel, or topoisomerase inhibitors, i.e., doxorubicin, camptothecin, and irinotecan.

The terms "Pac-PCat-RNAi", "Doc-PCat-RNAi", "Col-PCat-RNAi", and "Vin-PCat-RNAi" refer to PCat liposomes containing an RNAi agent and an enabler agent, where the corresponding enabler agent is paclitaxel, docetaxel, colchicine, and vincristine.

The term "vector" refers to a vehicle or other mechanism by which gene delivery or nucleic acid delivery can be accomplished. In certain embodiments, gene delivery or nucleic acid delivery, including RNAi agent delivery, can be achieved by a number of mechanisms including, for example, vectors derived from viral and non-viral sources, cation complexes, nanoparticles, liposomes, and the like.

The terms "carrier" and "vector" are used interchangeably, and refer to a vehicle. For example, an RNAi carrier refers to a vehicle for transport of RNAi, such as, for example, a liposome; an RNAi carrier liposome or an RNAi liposome carrier refers to a situation where a liposome is the carrier or vehicle of the RNAi; a pharmaceutically acceptable carrier is an art recognized term referring to a vehicle or medium for containing an agent, presumably a product with a therapeutic purpose.

The terms "drug" and "agent" are used interchangeably and refer to substance that is used for diagnosing, detecting, or monitoring tumors or proliferative disorders. The term "agent" includes small molecules, macromolecules (e.g., peptides, proteins, antibodies, or antibody fragments), nucleic acids (e.g., gene therapy constructs), recombinant viruses, nucleic acid fragments (including, e.g., synthetic nucleic acid fragments, siRNA molecules, antisense molecules), nanoparticles, and microparticles.

The terms "tubulin-active agent", "antitubulin", "anti-microtubule", "anti-tubulin agent", or "antimicrotubule agent" are as art-recognized and refer to a chemotherapeutic agent that blocks cell division by interfering with tubulins, microtubules, mitotic spindle, or mitosis process.

The term "topoisomerase inhibitor" is as art-recognized and refers to agents designed to interfere with the action of topoisomerase enzymes, which are enzymes that control the changes in DNA structure by catalyzing the breaking and rejoining of the phosphodiester backbone of DNA strands during the normal cell cycle.

The terms "sub-therapeutic", "sub-cytotoxic" and "non-cytotoxic" are used interchangeably, and refer to doses or concentrations that are lower than those typically used for treatment in humans or cause cytotoxicity to cultured cells used in the experiments. For example, a subtherapeutic dose in a human subject for paclitaxel is less than about 120 mg/m$^2$, for docetaxel is less than about 72 mg/m$^2$, for vincristine is less than about 1 mg/m$^2$, for colchicine is less than about 3 mg oral dose, and for doxorubicin is less than about 60 mg/m$^2$.

The term "apoptosis" refers to any non-necrotic, well-regulated form of cell death, as defined by criteria well established in the art.

The terms "vulnerable to endosome-lysosome transport or lysosomal degradation", or "subject to endosome-lysosome transport or lysosomal degradation" are used interchangeably, and referred to a propensity of rapid degradation of agents during endosome-lysosome transport or after entering the lysosomes in the cell. Examples of such agents that are subject to lysosomal degradation are oligonucleotide compounds, including antisense oligonucleotides, and gene therapy constructs, and various peptides and proteins.

The terms "cytosol" and "cytoplasm" are used interchangeably, as defined in the art.

Within certain embodiments of this disclosure, pharmaceutical compositions and methods are provided that feature the presence or administration of one or more RNAi molecules or other dsRNA or analogs thereof of this disclosure, possibly combined, complexed, or conjugated with a polypeptide, optionally formulated with a pharmaceutically-acceptable carrier, such as a diluent, stabilizer, buffer, or the like. The negatively charged dsRNA molecules of this disclosure may be administered to a patient by any standard means, with or without stabilizers, buffers, or the like, to form a composition suitable for treatment. When it is desired to use a liposome delivery mechanism, standard protocols for formation of liposomes can be followed. The compositions of the present disclosure may also be formulated and used as a tablet, capsule or elixir for oral administration, suppository for rectal administration, sterile solution, or suspension for injectable administration, either with or without other compounds known in the art. Thus, dsRNAs of the present disclosure may be administered in any form, such as nasally, transdermally, parenterally, or by local injection.

The terms "polyplexes" and "lipoplexes" refer to carriers for gene delivery or nucleic acid delivery, forming a condensed complex between negative polynucleotide molecules and positive carrier molecules. In lipoplexes, the cationic carrier molecule is a lipid molecule, for example a cationic phospholipid, for example DOTAP. In polyplexes, the carrier molecule is a non-lipid cation or polycation, for example polycations containing cyclodextrin, polyethyleneimime, polylysine, and polyhistidine. At times, cationic liposomes carrying polynucleotide molecules such as RNAi agents are also referred to as lipoplexes.

The term "liposome" refers to a generally spherical cluster or aggregate of amphipathic compounds, including lipid compounds, typically in the form of one or more concentric layers, for example, monolayers and/or bilayers. They may also be referred to herein as lipid vesicles. The liposomes may be formulated, for example, from ionic lipids and/or non-ionic lipids.

The term "cationic liposomes" are liposomes that contain lipid components that have an overall positive charge at physiological pH.

The term "neutral liposomes" are liposomes that contain lipid components that have an overall neutral charge at physiological pH.

The term "lipid" refers to a synthetic or naturally-occurring compound which is generally amphipathic and biocompatible. The lipids typically comprise a hydrophilic component and a hydrophobic component. Exemplary lipids include, for example, fatty acids, neutral fats, phosphatides, glycolipids, surface-active agents (surfactants), aliphatic alcohols, waxes, terpenes, and steroids.

The term "neutral lipid" refers to any of a number of lipid species which exist either in an uncharged or neutral zwitterionic form a physiological pH. Such lipids include, for example, diacylphosphatidylcholine, diacylphosphatidylethanolamine, ceramide, sphingomyelin, cephalin, cholesterol, cerebrosides and diacylglycerols. In one embodiment, certain neutral lipids, including cholesterol and other sterol derivatives, are known to increase the stability of liposomes and are referred to as "liposomes stabilizing lipids".

The term "DOTAP" refers to the cationic lipid molecule N-(1-(2,3-dioleoyloxy)propyl)-N,N,N-trimethylammonium chloride.

The term "DOPE" refers to the lipid molecule dioleoylphosphatidylethanolamine.

The term "DSPE" refers to the lipid molecule 1,2 distearoyl-sn-glycero-3-phosphoethanolamine.

The term "DSPE-PEG2000" refers to a molecule composed of DSPE covalently linked to PEG, where the molecular weight of the PEG polymer is about 2000 g/mole. Inclusion of DSPE-PEG2000 into the lipid composition of a liposome confers PEGylation to the liposome.

The terms "pegylated" or "PEGylated" are used interchangeably herein, and refer to modification of a liposome or molecule with one or more polyethylene glycol (PEG) side chains. Liposomes modified with PEG or PEG-derivatives are sometimes called "PEGylated liposomes." The process of preparing a PEGylated liposome is at times referred to as "PEGylation".

The terms "DC liposomes" and "PCat liposomes" refers to cationic liposome preparations capable of carrying RNAi agents. Specifically, the term "DC liposome" refers to the standard cationic liposomes comprising 50:50 DOTAP:Cholesterol, and the term "PCat liposomes" refers to the DOTAP:Cholesterol:DOPE: DSPE-PEG2000 liposomes for which the preparation is described in Example 1.

The terms "benign", "premalignant", and "malignant" are to be given their art recognized meanings.

The terms "cancer", "tumor cell", "tumor", "leukemia", or "leukemic cell" are used interchangeably and refer to any neoplasm ("new growth"), such as, for example, a carcinoma (derived from epithelial cells), adenocarcinoma (derived from glandular tissue), sarcoma (derived from connective tissue), lymphoma (derived from lymph tissue), or cancer of the blood (e.g., leukemia or erythroleukemia). The terms "cancer" or "tumor cell" also are intended to encompass cancerous tissue or a tumor mass, which shall be construed as a compilation of cancer cells or tumor cells, and are intended to encompass cancers or cells that may be either benign, premalignant, or malignant. Typically a cancer or tumor cell exhibits various art recognized hallmarks such as, for example, growth factor independence, lack of cell/cell contact growth inhibition, and/or abnormal karyotype. By contrast, a normal cell typically can only be passaged in culture for a finite number of passages and/or exhibits various art-recognized hallmarks attributed to normal cells (e.g., growth factor dependence, contact inhibition, and/or a normal karyotype). Genetically normal cells that are physically part of the aberrant growth and frequently play an integral role in the proliferative process are also referred to as cancer cells or tumor cells. This includes, inter alia, stromal and endothelial cells that proliferate under influence of tumor-secreted factors, and stromal cells that stimulate proliferation of epithelial tumor cells.

The term "cell" includes any eukaryotic cell, such as, for example, somatic or germ line mammalian cells, or cell lines, e.g., HeLa cells (human), NIH3T3 cells (murine), embryonic stem cells, and cell types such as hematopoietic stem cells, myoblasts, hepatocytes, lymphocytes, and epithelial cells and, e.g., the cell lines described herein.

The terms "peritoneal", "intraperitoneal", "peritoneally", or "intraperitoneally" are used interchangeably, and are related to the peritoneal or abdominal cavity.

The terms "peritoneal cavity" and "abdominal cavity" are used interchangeably.

The terms "locally", "regionally", "systemically" refer to, respectively, the administration of a therapy "locally", e.g., into a tumor mass for a cancer treatment, or into an organ or tissue for treatment of that organ or tissue, such as intravitreal administration for treatment of the eye, intrasynovial for treatment of a joint, etc., "regionally", e.g., in a general tumor field or an area suspected to be seeded with metastases for a cancer treatment, or, e.g., in a general field or area populated with a target organism or tissue for, e.g., an anti-infectious treatment, or "systemically", e.g., orally, intravenously, intramuscularly, subcutaneously, or by inhalation with the intent that the agent will be widely disseminated throughout the subject.

The term "pharmaceutically acceptable carrier" is art recognized and includes a pharmaceutically acceptable material, composition or vehicle, suitable for administering compounds of the present disclosure to mammals.

The term "pharmaceutical composition" includes preparations suitable for administration to mammals, e.g., humans. When the compounds of the present disclosure are administered as pharmaceuticals to mammals, e.g., humans, they can be given per se or as a pharmaceutical composition containing, for example, 0.1 to 99.5% (more preferably, 0.5 to 90%) of active ingredient (e.g., a therapeutically-effective amount) in combination with a pharmaceutically acceptable carrier.

The term "subject" is intended to include human and non-human animals (e.g., inter alia, mice, rats, rabbits, cats, dogs, livestock, and primates).

The term "microparticles" refers to particles of about 0.1 µm to about 100 µm, about 0.5 µm to about 50 µm, 0.5 µm to about 20 µm in size, advantageously, particles of about 1 µm to about 10 µm in size, about 5 µm in size, or mixtures thereof. The microparticles may comprise macromolecules such as RNAi agents, for example. Typically microparticles can be administered locally or regionally, for example.

The term "nanoparticles" refers to particles of about 0.1 nm to about 1 µm, 1 nm to about 1 µm, about 10 nm to about 1 µm, about 50 nm to about 1 µm, about 100 nm to about 1 µm. The nanoparticles may comprise macromolecules such as RNAi agents, for example. Typically, nanoparticles can be administered to a patient via local, regional, or systemic administration.

The term "particles" refers to nanoparticles, microparticles, or both nanoparticles and microparticles.

The terms "degrading" and "degradation" are used interchangeably, and refer to the decomposition of nanoparticles and microparticles or the decomposition of polymers or liposomes. Similarly, the terms could refer to the decomposition of RNAi agents, proteins, therapeutic agents and other chemical compounds, by enzymatic or non-enzymatic means.

The term "formulation" refers to the art-recognized composition where an agent is incorporated in a dosage form.

The term "tumor priming method" refers to a method of enhancing the penetration of an agent by "priming" the tumor with an apoptosis-inducing agent to decrease tumor cell density. The apoptosis-inducing agent may be used to enhance delivery of RNAi agents associated with the nanoparticles or microparticles, where the delivery of the nanoparticles or microparticles to the tumor tissue is enhanced, compared to when the pretreatment with the apoptosis-inducing agent is not used.

The terms "tumor penetrating particles" or "TPM" refers to nanoparticles or microparticles that are comprised of components that utilize the tumor priming method, such that the particles can penetrate deeper into tumors compared to nanoparticles or microparticles that are not comprised of a tumor priming component.

The term "PLGA", or "poly(lactide-co-glycolide)" refers to a copolymer consisting of various ratios of lactic acid or lactide (LA) and glycolic acid or glycolide (GA). The copolymer can have different average chain lengths, resulting in different internal viscosities and differences in polymer properties. PLGA is used for the preparation of microparticles or nanoparticles. Methods used to prepare these particles are described in, for example, Example 3 of application Ser. No. 11/242,546 cited above.

The terms "localize" and "concentrate" are used interchangeably, to indicate the preferential distribution at a specific site, e.g., tumor tissues.

The term "bioadhesive" means natural, synthetic or semi-synthetic substances that adhere and preferably and strongly adhere to a surface such as skin, mucous membrane, and tumor. Suitable bioadhesives include, for example, poly(l-ysine), fibrinogen, those prepared from partially esterified polyacrylic acid polymers, including polyacrylic acid polymers, natural or synthetic polysaccharides such as cellulose derivatives including methylcellulose, cellulose acetate, carboxymethylcellulose, hydroxyethylcellulose, pectin, and a mixture of sulfated sucrose and aluminum hydroxide.

The term "genetic disorder" means any disease that is caused by an abnormality in a subject's genome. The abnormality can range from minuscule to major—from a discrete mutation in a single base in the DNA of a single gene to a gross chromosome abnormality involving the addition or subtraction of an entire chromosome or set of chromosomes. Types of genetic inheritance include single inheritance (for example, cystic fibrosis, sickle cell anemia, Marfan syndrome, and hemochromatosis), multifactoral inheritance (for example, high blood pressure, Alzheimer's disease, cancer, arthritis, and diabetes), chromosome abnormalities (for example, Turner syndrome, and Klinefelter syndrome), and mitochondrial inheritance (for example, epilepsy and dementia).

The term "metabolic disorder" refers to a group of identified disorders in which errors of metabolism, imbalances in metabolism, or sub-optimal metabolism occur. Metabolic disorders as described herein also include diseases that can be treated through the modulation of metabolism, although the disease itself may or may not be caused by a specific metabolic defect. As example, type II diabetes is a metabolic disorder.

2. METHODS

In a first aspect, this disclosure provides a method to promote the delivery of an RNAi therapy agent into a tumor. This method involves the use of the tumor priming method, comprising of the delivery of the apoptosis-inducing agent and a formulation of the RNAi agent. The purpose of the apoptosis-inducing agent is to cause reduction of cell density, allowing enhanced delivery of the RNAi formulation into the tumor. The apoptosis-inducing agent requires a 24-96 hour lag time to exert the tumor-priming effect. The apoptosis-inducing agents produce substantial degree of apoptosis to cause a reduction in cell density of >30%, >20%, >10%, >4%, or >2%.

In certain embodiments, the RNAi agent is administered separately from the apoptosis-inducing agent, after apoptosis has been induced. The apoptosis inducing agent of the tumor-priming method is used as a pretreatment before the RNAi agent or its liposomal formulation is administered, and this pretreatment allows for enhanced delivery of the RNAi agent as compared to when the pretreatment is not used. A time duration ranging from between about a few hours to about 96 hours, or preferably from about 24 to about 72 hours, is allowed to elapse between the administration of the apoptosis-inducing agent and the RNAi agent.

In certain embodiments, the disclosure uses tumor-penetrating particles, which allow for the concomitant administration of the apoptosis-inducing agent and the RNAi agent. The apoptosis-inducing agent is formulated as a fast-release or a slow-release formulation, and the RNAi agent is formulated in a long-circulating or slow-release formulation. After administration, the rapid release formulation of apoptosis-inducing agent will result in apoptosis in the tissue and the long-circulating or slow-release formulation of RNAi will allow for delivery of the RNAi agent after a substantial degree of apoptosis has been achieved. The slow-release formulation of apoptosis-inducing agent provides sustained apoptosis in the tissue, facilitating the delivery of the RNAi agent. In a related embodiment, the RNAi agent, formulated in long-circulating or slow release formulation, is administered at about the same time as the apoptosis-inducing agent. Because of the long circulation time, the RNAi agent will be available to be delivered to the tumor at the time that apoptosis has occurred.

In one embodiment, this disclosure provides for a method to promote the delivery or penetration of an RNAi agent into a tumor located in the peritoneal cavity of a patient. In one embodiment, the RNAi agent is administered systemically.

In a second aspect, this disclosure provides for methods to promote the intracellular bioavailability of RNAi agents to a cell.

As shown in Example 7 of this disclosure, enabler agents that perturb the tubulin-microtubule dynamics and the enzymes topoisomerases, but not other cytotoxic agents with different action mechanisms, cause enhanced intracellular release of oligonucleotides, e.g., inter alia, siGLO, anti-K-ras siRNA, anti-survivin siRNA or anti-∃-catenin siRNA, carried in liposomes. The finding of increased intracellular bioavailability and increased activity of RNAi, resulting from the addition of enabler agents, is surprising and provides a solution to a major impediment for efficient RNAi transfection using nonviral vectors. It should further be realized that this method is different from the common approach in cancer chemotherapy of using a combination of two or more active treatments to achieve a combination treatment with greater activity, for at least three reasons. First, when combining standard chemotherapy with RNAi therapy, the objective is to achieve optimal activity of both treatments. As RNAi therapy achieves its goal of depletion of an endogenous protein by blocking the synthesis of this protein, a lag time or delay is expected between these two events due to the need of depleting the pre-existing proteins. For this reason, RNAi therapy is commonly given first, followed by addition of chemotherapy. In contrast, the current disclosure requires the administration of the enabler agent before, or at the same time as, the RNAi therapy. This is because the enabler agent acts to enhance the transfection efficiency of the RNAi (and hence the requirement of prior or simultaneous treatment). A second reason that the current method is different from the art of combining two or more active therapies is that the common practice is based on the consideration of additive and synergistic interaction of therapeutics that have on their own activity against the to-be-treated disease. In contrast, the current method teaches combinations using an RNAi agent, such as anti-survivin siRNA that is inactive by itself, or using the enabler agent paclitaxel at concentrations or exposures that have no cytotoxicity (see Example 9). The instant disclosure of that such combinations can yield effective RNA interference, therefore, is different and cannot be anticipated from the art. The third reason that the current method is different from the art of combining two or more active therapies is, as shown in Example 7, only selected classes of agents such as tubulin-active agents and topoisomerase inhibitors, but not DNA-active agents such as cisplatin or antimetabolites such as 5-fluorouracil, are able to improve the delivery, release and transfection of RNAi agents. This finding means that RNAi agents cannot be routinely or non-discriminatively combined with chemotherapeutics.

In one embodiment, the RNAi agent is an siRNA, an miRNA, or an shRNA.

In certain embodiments, the RNAi agent and the enabler agent are administered by different schedules. A cell is treated with an enabler agent for 1, 2, 4, 8, 12, or 24 hours before the cell is treated with the RNAi agent. A cell is treated with the enabler agent and the RNAi agent concurrently, either in two separate preparations or jointly in one formulation, e.g., inter alia, the same PCat liposome formulation.

In certain embodiments, the enabler agent is one or more of any of the clinically used tubulin-active agents, including, inter alia, paclitaxel, docetaxel, cabaxitaxel, vincristine, vinblastine, vinorelbine, amphethinile, maytansine, cemadotin, rhizoxin, methyl N-[6-(3,4,5-trimethoxybenzyloxy)imidazo (1,2b)-pyridazin-2-yl]carbamate, CI-980, dolastatin, desoxyepothilone, discodermolide, epothilone B lactam, 21-aminoepothilone B, BMS-310705, BMS-184476, BMS-188791, RPR 109881A, patupilone, TXD 258, Combretastatin A-4 phosphate, halichondrin B, ZD 6126, Vinflunine, LU103793, E7010, E7389, E-7070, T138067, T900607, epothilone analog, patupilone, ixabepilone, discodermolide, eribulin, cryptophycin, desacetyl vinblastine amide, ecteinascidin, combretastatins, IDN-5109, D-24851, D-64131, ZK-EPO or colchicine. The tubulin-active agent can also be one or more of any of the tubulin-active agents that are used in preclinical application, including, inter alia, nocodazole, hemiasterlin, sarcotidicytins A and B, eleutherobin, laulimalide, isolaulimalide, marine soft-coral-derived natural products, marine-derived microtubule-stabilizing agents, mivobulin, isethionate.

In certain embodiments, the tubulin-active agent is paclitaxel, docetaxel, vincristine, or cabazitaxel. A cell is exposed to a drug concentration of 0.1-100 nM, 0.1-50 nM, 0.1-20 nM, 0.1-10 nM, or 0.1-2 nM. A cell is exposed to a drug concentration-time product of less than 1200 nM-hr, 600 nM-hr, 400 nM-hr, 240 nM-hr, 120 nM-hr, 60 nM-hr, 40 nM-hr, 20 nM-hr, or 10 nM-hr.

In certain embodiments, the tubulin-active agent is colchicine or nocodazole. A cell is exposed to a drug concentration of 1-1000 nM, 1-500 nM, 1-200 nM, or 1-100 nM. A cell is exposed to drug concentration-time product of less than 12000 nM-hr, 6000 nM-hr, 4000 nM-hr, 2400 nM-hr, 1200 nM-hr, 600 nM-hr, 400 nM-hr, 200 nM-hr, or 100 nM-hr.

In certain embodiments, the enabler agent is one or more of the topoisomerase inhibitors. Examples of topoisomerase II inhibitors include doxorubicin, etoposide, amsacrine, teniposide, ICRF 193, dexrazoxane, ellipticine, epirubicin, merbarone, mitoxantrone, pirarubicin, podophyllotoxin, and sobuzoxane. Examples of topoisomerase I inhibitors include irinotecan, topotecan, camptothecin, lamellarin D, 2',3'-dideoxyadenosine-5'-triphosphate, β-lapachone, cytosine β-D-arabinofuranoside, 10-hydroxycamptothecin, and netropsin.

A cell is exposed to a doxorubicin concentration of 0.1-100 nM, 0.1-50 nM, 0.1-20 nM, or 0.1-10 nM. A cell is exposed to a doxorubicin concentration-time product of less than 1200 nM-hr, 600 nM-hr, 400 nM-hr, 240 nM-hr, 120 nM-hr, 60 nM-hr, 40 nM-hr, 20 nM-hr, or 10 nM-hr.

In certain embodiments, the enabler agent is formulated in a pharmaceutically acceptable carrier. In an embodiment, the common clinical formulation is used. In another embodiment, the formulation is nanoparticles that are preferentially delivered to the tumor. In another embodiment, the formulation is nanoparticles that release the tubulin-active agent rapidly. In a related embodiment, the nanoparticles release more than 10%, 20%, 30%, 40%, 50% or 60% of its contents of an apoptosis-inducing agent within one day and causes inhibition of tubulin function in the tissue.

In a preferred embodiment, an effective concentration of an enabler agent is maintained in the tissue during the administration of the RNAi therapy agent.

The methods of the disclosure can be used to effectively treat diseases characterized by overexpression of the gene corresponding to the RNAi, by increasing the intracellular bioavailability of RNAi agents in the cell and thus increasing the therapeutic effect of the RNAi treatment.

In the third aspect, this disclosure provides methods to enhance the delivery of RNAi agents to cells in solid tumors and to enhance the intracellular bioavailability of RNAi agents. This is accomplished through the combined application of one or more apoptosis-inducing agents and one or more enabler agents. Administration of the apoptosis-inducing agent will occur before or simultaneously with administration of the enabler agent. The purpose of the apoptosis-inducing agent is to reduce cell density, allowing enhanced delivery of the RNAi formulation into the tumor. The purpose of the enabler agent is to promote the release of the RNAi agent from its carriers, endosomes and lysosomes.

In one embodiment, administration of the enabler agent is repeated to maintain the tubulin-active or topoisomerase-inhibitory concentrations during administration of RNAi therapy.

In one embodiment, the apoptosis-inducing agent is different from the enabler agent. Examples of apoptosis-inducing agents include agents such as paclitaxel, vincristine, vinblastine, vindesine, vinorelbin, taxotere (Docetaxel®), cabazitaxel, doxorubicin, topotecan, camptothecin, irinotecan hydrochloride (Camptosar®), etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C®), trimetrexate, gemcitabine, acivicin, alanosine, pyrazofurin, N-Phosphoracetyl-L-Asparate (PALA®), pentostatin, 5-azacitidine, 5-Aza-2'-deoxycytidine, adenosine arabinoside (ARA-A®), cladribine, ftorafur, UFT® (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax®), flutamide, 4'-cyano-3-(4-fluorophenylsulphonyl)-2-hydroxy-2-methyl-3'-(trifluoro-methyl)propionanilide, Herceptin®, anti-CD20 (Rituxan®), interferon alpha, interferon beta, interferon gamma, interleukin 2, interleukin 4, interleukin 12, tumor necrosis factors, and radiation. Examples of enabler agents are tubulin-active agents and topoisomerase inhibitors.

In certain embodiments, the apoptosis-inducing agent is also an enabler agent. In order to fulfill the combined function of priming and enhanced intracellular bioavailability, the agent is maintained at apoptosis-inducing concentrations during the initial phase of use. Subsequently, at the time of administration or availability of the RNAi therapy, the enabler agent is maintained at concentrations capable of enhancing the release of an RNA agent from its carriers, endosomes or lysosomes. Examples of these dual-function agents are paclitaxel, docetaxel, cabazitaxel, vincristine, and doxorubicin.

In a fourth aspect, this application discloses methods for enhancing the intracellular bioavailability of therapeutic agents that are subject to endosome-lysosome transport or to lysosomal degradation.

In certain embodiments, the methods comprise combining enabler agents and said therapeutic agents, where the use of enabler agent enhances the intracellular bioavailability of said therapeutic agents relative to without enabler agent.

Examples of said therapeutic agents are RNAi agents, antisense oligonucleotides, gene constructs, peptides and proteins. Administration of said therapeutic agents and enabler agents is as above-described for administration of RNAi agents and enabler agents.

In certain embodiments, the enabler agents, the therapeutic agents subject to endosome-lysosome transport or to lysosomal degradation, are further combined with apoptosis-inducing agents, in order to enhance the delivery of said therapeutic agents to cells in a multi-layered tissue such as a solid tumor. These agents are administered as above-described for combinations of RNAi agents, enabler agents, and apoptosis-inducing agents, either separately in different formulations, concurrently in different formulations, or jointly in the same formulations. The following is offered as an example of a separate administration of combinations comprising all three agents. Administration will be by applying initially the pre-treatment with the apoptosis-inducing agents. When sufficient time has passed for apoptosis to be induced and cell density to be reduced, i.e., generally about 24-96 hours, the enabler agent is administered, and the RNAi agent is administered either concurrently with the enable agent or after a delay of a few hours.

In one embodiment, the apoptosis-inducing agent is formulated in rapid-release and slow-release particles. The method for administering said particles, in combination with the enabler agent and the therapeutic agent subject to endosome-lysosome transport or to lysosomal degradation, will be as above-described in the method to administer the combination of said particles with RNAi agents. In one embodiment, said therapeutic agent is formulated in long-circulating liposomes or slow-release formulations to allow delivery of the therapeutic agent, in which case the combination of said therapeutic agent and apoptosis-inducing agent can be administered at the same time.

In the fifth aspect, the disclosure describes a method for RNAi transfection of cells cultured in vitro, comprises the steps of:

(a) contacting the cells with one or more of the enabler agents, and (b) treating the cells with a liposomal RNAi preparation.

In certain embodiments, the cells are contacted with sufficient concentrations of one or more of enabler agents to enhance the intracellular bioavailability of RNAi agents. The contacting of the cell with the enabler agent can be before, or at about the same time, as the contacting of the cells with the RNAi agent.

In a preferred embodiment, the enabler agent is one or more of the tubulin-active agents (e.g., inter alia, paclitaxel, docetaxel, vincristine, colchicine or nocodazole), or the topoisomerase inhibitors (e.g., inter alia, doxorubicin). For paclitaxel, docetaxel, cabazitaxel, vincristine, or doxorubicin a concentration of about 10 nM is maintained for about 1, 2 or 4 hours. For colchicine or nocodazole, a concentration of about 10 nM is maintained for about 1, 2 or 4 hours.

3. COMPOSITIONS

In the instant disclosure, RNAi agents are formulated in liposomes, and administered either alone, in combination with apoptosis-inducing agents to achieve increased delivery through tumor-priming, in combination with enabling agents to achieve increased intracellular delivery through enhanced release from its carriers, endosomes or lysosoems, or in combination with both apoptosis-inducing agents and enabling agents. The apoptosis-inducing agents and enabling agents described herein may be formulated in a conventional manner using one or more physiologically acceptable carriers or exceptions. For example, these compounds and their physiologically acceptable salts and solvates may be formulated for administration, e.g., inter alia, by injection by the intravenous route, intraperitoneally, or subcutaneously. In one embodiment, an apoptosis-inducing agent or enabling agent may be administered locally, at the site where the target cells are present. The RNAi agents, apoptosis-inducing agents, and enabling agents can be formulated for a variety of modes of administration, including systemic or localized administration. For injection, the compounds can be formulated in liquid solutions or suspensions, preferably in physiologically compatible buffers or in physiologic saline. In addition, the compounds may be formulated in solid form and redissolved or suspended immediately prior to use. Lyophilized forms are also included. The compounds may be formulated for parenteral administration by injection, e.g., by bolus injection or continuous infusion. Formulations for injection may be presented in unit dosage form, e.g., in ampoules or in multi-dose containers, with an added preservative. Additional formulation forms and compositions are described in the following aspects.

In a sixth aspect, this disclosure provides for compositions to be used for apoptosis-inducing agents.

In certain embodiments, the apoptosis-inducing agent is any of the apoptosis-inducing agents of the art and the agent is used in its common clinical formulation. In a preferred embodiment, the apoptosis-inducing agent is paclitaxel, docetaxel, cabazitaxel, or doxorubicin, and is formulated in one of the common clinical formulations, e.g., inter alia, Taxol®, Abraxane®, Taxotere®, Jevtan®, doxorubicin, Doxil®.

In one embodiment, the apoptosis-inducing agents are formulated in drug-loaded PLGA particles that release the apoptosis-inducing agent over time.

In certain embodiments, the drug-loaded PLGA particles consist of a fast-release component, which releases greater than 10%, 20%, 30%, 40%, 50%, or 60% of its contents of an apoptosis-inducing agent within one day and causes apoptosis in the tissue, and further consists of one or more slow-release components, which maintain release of the apoptosis-inducing agent for several days, several weeks or longer. The combination of the two components provides a better controlled drug release, consisting of a rapid early release followed by a protracted later release, than can be obtained by a single formulation with an early burst release. The apoptosis-inducing agent can be any of the apoptosis-inducing agents of the art, and is preferentially paclitaxel or docetaxel. The PLGA particles are microparticles or nanoparticles. A typical formulation will contain no more than 30%, 15%, 10%, 5%, 4%, 3%, or 1% of the total weight of the formulation in the form of the agent. At times, it is advantageous to add a release enhancer, such as Tween 20, Tween 80, isopropyl myristate, β-lactose, or diethyl phthalate, in order to achieve a release rate as desired for the application. Exemplary particles are, for example, fast-release PLGA particles made of 50:50 lactide:glycolide, having an average diameter of between 4 to 6 µm, a glass transition temperature that is below the body temperature (e.g., 30° C.), a ~4% load of paclitaxel, and a drug release rate of ~70% in one day. Exemplary slow-release PLGA particles are made of 75:25 lactide:glycolide, have an average diameter of between 3 to 6 µm, a glass transition temperature that is above the body temperature (e.g., 50° C.), a ~4% load of paclitaxel, and an initial burst drug release rate of ~5% in the first day, followed by a slower release yielding a total cumulative release of 30% in seven weeks. The PLGA particles with a glass transition temperature (Tg) below the body temperature enhance the selective adhesion of the particles to tumor tissue. Adhesion of particles to tumor tissue also can be obtained by increasing their bioadhesive properties using cross-linking with poly(lysine), by coating the particles with fibrinogen, or by other art-recognized methods. Particles of this size and further physical characteristics are well-suited for regional delivery, for example for intraperitoneal delivery. Similar particles of smaller size, preferably smaller than 200 nm, 150 nm, 100 nm, 80 nm can be contemplated for intravenous administration. The apoptosis-inducing agent is formulated in nanoparticles that are preferentially delivered to the tumor.

In a seventh aspect, this disclosure provides for compositions of RNAi carriers. The difficulty of formulating effective liposomal preparations for delivery of RNAi agents stems from the many, at times conflicting, functions the carrier needs to fulfill for efficacy. For example, the lipid carrier needs to bind or complex the RNAi agent, protect the RNAi agent from elimination, avoid particle aggregation, avoid removal by the reticular endothelial system, present minimal toxicity, reach the target tissue, reach the target cell, enter the target cell, escape from endosomes and from lysosomal breakdown, and release the RNAi agent intact in the cytosol to exert its RNA interference activity. Navigation among these many determining factors has proven a nearly insurmountable barrier to development of clinically applicable carriers, as discussed in Statement of problems.

In order to identify a useful RNAi formulation, an investigator will need to select from a multitude of possibilities. For example, various forms of carriers including liposomes, microemulsions, emulsions, micelles, nanoparticles, nanospheres, nanocapsule, pharmacosomes, and polymersome were contemplated by Applicants. After liposomes are selected, a large number of choices remain. For example, the main components of liposomes frequently fall in at least four categories: cationic lipids, neutral phospholipids, PEGylated lipids, and stabilizing lipids. Cationic lipids have the advantage of complexing and protecting RNAi molecules. Many cationic lipids have been described in the art, and include, for example, 1,2-dioleoyl-3-trimethylammonium-propane (DOTAP), N-[1-(2,3-Dioleoyloxy) Propyl]-N,N,N-trimethylammonium Chloride, N-[2,3-(dioleyloxy)propyl]-N,N,N-trimethylammonium (DOTMA), $N^1$-cholesteryl-oxycarbonyl-3,7-diazanonane-1,9-diamine (CDAN), 3β[I-ornithinamide-carbamoyl]cholesterol (O-Chol), a carbamate-linked polyamine cholesterol derivative, dioleyl-N,N-dimethylammonium chloride (DODAC), Dimethyldioctadecylammonium, N,N-distearyl-N,N-dimethyl-ammonium bromide (DDAB), 3β-(N—(N',N'-dimethylamino-ethane)-carbamoyl)cholesterol (DC-Chol), N-(1,2-dimyristyloxyprop-3-yl)-N,N-dimethyl-N-hydroxyethyl ammonium bromide (DMRIE), 1,2-dilauroyl-sn-glycero-3-ethylphosphocholine, N-(1-(2,3-dioleyloxy)propyl)-N-(2-(sperminecarboxamido)ethyl)-N,N-dimethyl-ammonium trifluoroacetate (DOSPA), dioctadecylamidoglycyl carboxyspermine (DOGS), N-(2,3-dioleyloxy)propyl)-N,N-dimethylammonium chloride (DODMA), and 1,2-Dioleoyl-3-dimethylammonium-propane (DODAP). Alternatively, other cationic molecules can be integrated in the lipid bilayers to bind the RNAi agents. For example, cationic polymers and dendrimers, such as, inter alia, poly-L-lysine, polyethyleneimine (PEI), poly-D,L-lactide-co-glycolide (PLGA), chitosan, gelatin, poly(alkylcyanoacrylate), polyamidoamine (PAMAM), Poly(propyleneimine) (PPI), and cyclodextrin-containing cationic polymers. Out of these more than 16 possibilities, Applicants selected DOTAP as the cationic lipid in the RNAi delivery system, PCat. The art indicates that the use of DOTAP is problematic. For example, DOTAP-containing liposomes are associated with toxicity through inflammatory reactions and initiation of immune responses (e.g. (Wu, *AAPS. J.,* 11, 639, 2009), and DOTAP-containing liposomes used by Landen et al. were shown not to reach the target cells for their therapeutic action (Landen, Jr., *Cancer Res.,* 65, 6910, 2005b). Therefore, the art teaches away from the use of DOTAP. Hence, the current discovery that DOTAP-containing liposomes provide effective and safe delivery of RNAi is surprising and unexpected.

Neutral phospholipids are known in the art to have less toxicity, but can attenuate cellular uptake or decrease siRNA loading efficiency. Neutral liposomes and cationic liposomes show different pharmacokinetics, biodistribution, uptake and intracellular trafficking mechanisms. Neutral liposomes are less susceptible to interaction with negative constituents in the circulation after systemic delivery, compared to cationic liposomes. Cationic liposomes bind to and are taken up by endothelial cells after systemic delivery, while anionic and neutral liposomes are generally not. Positively charged liposomes bind to negatively charged cell surface constituents (e.g., heparin sulfate proteoglycans and integrins) and trigger cellular uptake mainly by endocytosis. Again, many neutral phospholipids are known in the art, and include egg phosphatidylcholine (EPC), dilauryloylphosphatidylcholine (DLPC), dimyristoylphosphatidylcholine (DMPC), dipalmitoylphosphatidylcholine (DPPC), distearoylphosphatidyl-choline (DSPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1-stearoyl-2-palmitoyl phosphatidylcholine (SPPC), dimyristyl phosphatidylcholine (DMPC), 1,2-distearoyl-sn-glycero-3-phosphocholine (DAPC), 1,2-diarachidoyl-sn-glycero-3-phosphocholine (DBPC), 1,2-dieicose-noyl-sn-glycero-3-phosphocholine (DEPC), palmitoyloeoyl phosphatidylcholine (POPC), lysophosphatidylcholine, dilinoleoylphosphatidylcholine, dioleoylphosphatidyl-ethanolamine (DOPE), distearoylphophatidylethanolamine (DSPE), dimyristoyl phosphatidylethanolamine (DMPE), dipalmitoyl phosphatidylethanolamine (DPPE), palmitoyloeoyl phosphatidylethanolamine (POPE), and lysophosphatidylethanolamine. Among these 22 possibilities, Applicants selected DOPE.

The lipid cholesterol often is added to liposomal preparations, and is said to improve liposomes stability, increasing the lifetime in storage. Reasons for this stabilization are poorly understood. Applicants included cholesterol as a liposomes stabilizing lipid in a new cationic liposomal formulation.

Since the discovery that long, flexible chains of hydrophilic polymers, attached to liposomes as surface modifiers, reduce the interaction with plasma proteins, minimize recognition of the liposomes by the RES system and extend circulation time, a large number of such hydrophilic polymers have been produced. Most commonly, the hydrophilic polymer is poly-ethylene glycol (PEG) and is conjugated to a lipid for anchoring in the lipid bilayer of the liposome. For example, a commercial supplier of polyethylene glycol-conjugated lipids for application in liposomes provides 15 different PEGylated lipids on its website (NOF Corporation, Http://Www-.Phospholipid.Jp/Phospholipid_2-3.Html, 2010), including, inter alia, N-(carbonyl-methoxypolyethyleneglycol 2000)-1, 2-distearoyl-sn-glycero-3-phosphoethanolamine (DSPE-PEG 2000), and N-(carbonyl-methoxypolyethyleneglycol 5000)-1,2-distearoyl-sn-glycero-3-phosphor-ethanolamine (DSPE-PEG 5000). Other PEGylated lipids include, inter alia, cholesterol-anchored PEGs. The choice of PEGylated lipids affects liposome properties such as circulation time after administration in a subject.

Other ingredients that are added to liposomes to improve their performance in one area are also often at the detriment of performance in another area, are, among others, MPG (a peptide derived from the hydrophobic fusion peptide domain of HIV-1 gp41 protein and the hydrophilic nuclear localization sequence of SV40 large T antigen), TAT peptide or TAT-derived oligocarbamate.

Development of an effective liposomal carrier then requires selection of ingredients from among >16 cationic lipids, >22 neutral phospholipids, and >15 PEGylated lipids, for a total number of >5280 combinations. Within the selected ingredients, a large number of concentrations can be selected. For example, liposomal particles containing a 0%, 1%, 2%, 5%, and >5% PEGylated lipids have distinctly different characteristics. A conservative estimate of the number of potential combinations of four components, at five possible concentrations each, are more than 660,000 (multiplication product of $5280\times5^3$). The number of $5^3$ was used instead of $5^4$ because the concentration of the fourth component is fixed once the concentrations of the other three components have been selected. This large number of more than 660,000 possible combinations indicates that even though the art teaches the general principles of the advantages and disadvantages of the various lipid components, an artisan of ordinary skills will not be able to identify an effective RNAi carrier without extensive experimentation. Hence, Applicants' discovery that a specific liposomal formulation is an effective RNAi carrier for in vivo applications cannot be readily anticipated based on the art.

In certain embodiments, the RNAi agent is formulated in liposomal carriers. In one embodiment, the RNAi agent is formulated as RNAi-loaded liposome complexes or nanoparticles. The composition of the RNAi carrier liposomes comprises one or more of cationic lipids, one or more of neutral phospholipids, one or more of liposome stabilizing lipids, and one or more of PEGylated lipids. In one embodiment, the composition of the RNAi carrier liposomes of this disclosure comprises the cationic phospholipid DOTAP, the neutral phospholipids DOPE, the liposome stabilizing lipids cholesterol, and the PEGylated lipid DSPE-PEG2000. In a preferred embodiment, the molar proportions of DOTAP, cholesterol, DOPE and DSPE-PEG2000 is about 50:30:19:1.

In a most preferred embodiment, the composition of the RNAi carrier liposomes is the composition of the PEGylated liposomes PCat described in Example 1.

In an embodiment, the charge ratio between RNAi agent and cationic lipids is between 1:1 and 1:10, between 1:3 and 1:6, or about 1:4.

In one embodiment, the RNAi agent is not released from the formulation until after uptake of the liposomal carrier by the cell.

In one embodiment, the liposomes are of a final size of about 1000 nm, 800 nm, about 600 nm, about 400 nm, about 200 nm, about 150-180 nm, about 120-140 nm, about 100-120 nm, about 100 nm, about 50 nm, or about 20 nm.

In an embodiment, the RNAi carrier liposomes are combined with pharmaceutically acceptable excipients.

In certain embodiments, the RNAi agent is formulated in a lipid vesicle or liposomal carrier. The formulation preferably is prepared from a mixture of positively charged lipids, neutral lipids, cholesterol or a similar sterol, and negatively charged lipids. The positively charged lipids can be one of the cationic lipids known in the art, for example DOTAP, DOTMA, or analogs thereof. Neutral and negatively charged lipids can be any of the natural or synthetic phospholipids or mono-, di-, or triacylglycerols. The natural phospholipids are typically those from animal and plant sources, such as phosphatidylcholine, phosphatidylethanolamine, sphingomyelin, phosphatidylserine, or phosphatidylinositol. Synthetic phospholipids typically are those having identical fatty acid groups, including, but not limited to, dimyristoylphosphatidylcholine, dioleoylphosphatidylcholine, dipalmitoylphosphatidylcholine, distearoylphosphatidylcholine and the corresponding synthetic phosphatidylethanolamines and phosphatidylglycerols. The neutral lipid can be phosphatidylcholine, cardiolipin, phosphatidylethanolamine, mono-, di- or triacylglycerols, or analogues thereof. The negatively charged lipid can be phosphatidylglycerol, phosphatidic acid or a similar phospholipid analog. Other additives such as cholesterol, glycolipids, fatty acids, sphingolipids, prostaglandins, gangliosides, neobee, niosomes, or any other natural or synthetic amphophiles can also be used in liposome formulations, as is conventionally known for the preparation of liposomes.

In a formulation for preparing cationic lipid vesicles, the cationic lipid can be present at a concentration of between about 0.1 mole % and 100 mole %, 25 to 65 mole %, or between 40 and 60 mole %. The neutral lipid can be present in a concentration of between about 0 and 99.9 mole %, 0 to 50 mole %, or 15 to 35 mole %. In order to produce lipid vesicles or liposomes having a net positive charge, the quantity of the positively charged component must exceed that of the negatively charged component. The negatively charged lipid can be present at between about 0 to 49 mole % or 0 to 40 mole %. Cholesterol or a similar sterol can be present at 0 to 80 mole %, 20 to 60 mole % or 30 to 50 mole %.

Lipid formulations comprising at least one amphipathic lipid can spontaneously assemble to form primary liposomes, heterogeneous in size. Therefore, according to a preferred method, the lipid reagents of the invention, comprising at least one cationic lipid species, are prepared as liposomes according to the procedure of Example 1. The component lipids are dissolved in a solvent such as chloroform and the mixture evaporated to dryness as a film on the inner surface of a glass vessel. On suspension in an aqueous solvent, the amphipathic lipid molecules assemble themselves into primary liposomes. If other molecules are present in the aqueous solvent, such as, for example, a bioactive substance, these will be captured within the liposomes. Otherwise, empty liposomes will be formed.

Liposomes are reduced to a selected mean diameter by means of freeze-thawing. The liposome formulations of the invention are formed into vesicles of uniform size prior to transfection procedures, according to methods for vesicle production published in the literature and known to those in the art, for example, the sonication of spontaneously formed liposomes comprised of the lipids in aqueous solution described by Felgner (Felgner, *Proc. Natl. Acad. Sci. U.S.A*, 84, 7413, 1987). To prepare liposomes suitable for physiological in vivo use, having a unilamellar structure and a uniform size of from about 50 to about 200 micrometer in diameter, the primary liposomes are preferably processed by the freeze-thaw and extrusion processes.

An RNAi agent can be incorporated in the liposomes, inter alia, by allowing direct combination of the anionic RNAi molecules and the cationic liposomes in an aqueous medium. Other methods of the art can be used.

In an eighth aspect, this disclosure provides for compositions to be used for enabler agents.

In certain embodiments, the enabler agent is one ore more of the tubulin-active agents or topoisomerase inhibitory agents of the art. In a preferred embodiment, the enabler agent is paclitaxel, docetaxel, cabazitaxel, vincristine, colchicine, nocodazole, or doxorubicin. The enabler agent and the agent is formulated in one of the clinical formulations. The enabler agent is formulated as a simple solution, e.g., for use in in vitro transfection experiments. The enabler agent is prepared in formulations such as nanoparticles. The enable agent is prepared in rapid-release and slow-release particles such as those above-described for apoptosis-inducing agents.

Preparation of liposomes containing an enabler agent can use any of the methods known in the art. For example, a number of liposomal formulations for paclitaxel have been described. The encapsulation capacity of the conventional liposomal formulations for paclitaxel was about 3 mol %, which can be further increased to 7% by using pocket-forming lipids in the liposome formulation using methods of the art (Koudelka, *J. Pharm. Sci.,* 99, 2309, 2010). PEGylation of the liposome can inhibit the drug release from the liposomes and improve the stability of liposomes in plasma. The conventional and PEGylated liposomes released 55% and 33% of paclitaxel within 24 hours, and released less than 30% and 20% of paclitaxel within 6 hours of dialysis at room temperature, respectively (Yang, *Int. J. Pharm.,* 338, 317, 2007). Liposomal formulation can increase the elimination half-life of paclitaxel (Cabanes, *Int. J. Oncol.,* 12, 1035, 1998). Following intravenous injection, the terminal half-life for paclitaxel in the usual clinical formulation (Taxol®), conventional and PEGylated liposomal paclitaxel was 1.65, 5.05, and 17.8 hours, respectively; and the maximum tumor drug concentration was achieved within 6 hr for both conventional and PEGylated paclitaxel liposome formulations (Yang, 2007). In another example, a liposomal formulation for doxorubicin, Doxil®, is well known in the art, and is used clinically. Generally, most agents can be formulated in liposomes.

Several examples of liposomal preparations combining an enabler agent and an RNAi agent are provided in Example 1.

In one embodiment, a liposomal formulation contains an enabler agent in a weight ratio to the total weight of lipids of 1%, 0.4%, 0.2%, 0.1%, 0.06%, 0.04%, 0.02%, 0.01%, or 0.005%.

In a related embodiment, the enabler agent is paclitaxel, and the paclitaxel exposure to the cells is by a paclitaxel concentration of 0.1-100 nM, 0.1-50 nM, 0.1-20 nM, or 0.1-10 nM.

In an ninth aspect, this disclosure provides for compositions, comprising combinations of one or more of enabler agents with RNAi vectors. The combinations are termed RNAi delivery and expression system (RIDES). RIDES comprises two components. One component is the RNAi agent. The second component is one or more of enabler agents. The combined use of the two RIDES components enhances the intracellular bioavailability and transfection of RNAi agents and the effectiveness of RNAi.

In certain embodiments, the two RIDES components are formulated in a single entity. For example, an RNAi agent is formulated in liposomes and the enabler agent is co-formulated in the same liposomes, so that the RNAi agent and the enabler agent are administered simultaneously to the subject. Several examples of the single liposomal formulation containing both an RNAi agent and an enabler agent are shown in Example 1.

In certain embodiments, the two RIDES components are formulated in two different preparations and given separately. For example, the RNAi therapy agent is formulated in liposomes and the enabler agent is formulated in another formulation, where the two agents are administered to a subject at the same time or at different times. In one embodiment, the enabler agent is administered before the RNAi agent. Examples of liposomal preparations that provide effective delivery of RNAi agent are the PCat liposomes of Example 1.

In one embodiment, the RNAi agent is formulated in liposomes and the enabler agent is formulated in a pharmaceutically acceptable formulation, where the formulations for the RNAi agent and the enabler agent are combined before administration, and administration is to a cell, where the cell can be a cell in a cell culture, or in a subject.

In another embodiment, the RNAi agent is formulated in a vector of the art different from a cationic liposome. For example, said vector can be a polyplex, a neutral liposome, a viral vector, or another carrier that can be loaded with an RNAi agent, and can be transported into a cell.

In a tenth aspect, this disclosure provides for a kit for RNAi transfection, comprising instructions describing the method for RNAi transfection of cells cultured in vitro, and materials needed to perform the transfection.

In certain embodiments, the kit comprises materials include RNAi agents, liposomal lipids or liposomes, enabler agents, buffers, diluents, pipettes, or other necessary reagents. In one embodiment, these materials comprise premeasured amounts of RNAi agents, liposomal RNAi vectors, enabler agents, buffers and diluents. In a more preferred embodiment, these materials will comprise of premeasured amounts of RNAi agents, liposomal RNAi vectors that contain enabler agents, buffers and diluents.

In certain embodiments, the kit is for transfecting cells cultured in vitro or cells in a subject. Quantities of the components of the kit will depend on the type of experiments to be performed. As an example, for transfecting cells in culture, the quantities could be the quantities used for experiments of Examples 7-12. For transfecting cells in a subject, e.g., a laboratory mouse, the quantities could be the quantities used for experiments of Examples 3-4.

In certain embodiments, the kit comprises instructions and materials as described above, but without the RNAi agent. This is because RNAi is generally unstable, due to its rapid degradation by the omnipresent nucleases. Another reason is that a user may customize the RNAi agent to be incorporated in the RNAi vector liposomes. The kit will contain instructions on adding the to-be-tested RNAi agent to the liposomes to obtain the final liposomal RNAi product.

In an eleventh aspect, this application discloses compositions of combinations of therapeutic agents that are subject to endosome-lysosome transport or to lysosomal degradation.

In certain embodiments, the compositions comprise combinations of enabler agents and said therapeutic agents. Examples of said therapeutic agents are RNAi agents, antisense oligonucleotides, gene constructs, peptides and proteins. Said therapeutic agents generally are most advantageously formulated in liposomal formulations, to gain protection from rapid degradation in biological milieus. An example is the PCat liposomal formulation described in Example 1 for RNAi agents. Administration of said therapeutic agents and enabler agents is as above-described for administration of RNAi agents and enabler agents.

In certain embodiments, the enabler agents and the said therapeutic agents are further combined with apoptosis-inducing agents. These compositions comprise the above-described formulations for the respective agents. These compositions are administered as above-described for the RNAi agents, enabler agents, and apoptosis-inducing agents, either separately in different formulations, concurrently in different formulations, or jointly in the same formulations. The following is offered as an example of separate administrations of a combination comprising all three agents. Administration will be by applying initially the pretreatment with the apoptosis-inducing agents. When sufficient time has passed for apoptosis to be induced and cell density to be reduced, i.e., generally about 24-96 hours, the enabler agent is administered, and the RNAi agent is administered either concurrently with the enable agent or after a delay of a few hours.

In one embodiment, the composition consists of a fast-release formulation of an apoptosis-inducing agent, combined with a slow-release formulation of an enabler agent, and combined with long-circulating liposomes containing said therapeutic agent. In another embodiment, the apoptosis-inducing agent is formulated in a combination of rapid-release and slow-release particles.

4. EXEMPLARY USES

In certain aspects, the methods and compositions disclosed in the instant application are suitable for treating a disease that is caused by a faulty gene or the protein derived thereof. In one aspect, the disease can be a cancer, a metabolic, infectious, inflammatory, hormonal, or genetic disorder. In another aspect, the to-be-treated subject is genetically predisposed to a disease.

In certain embodiments, the cells with a faulty gene is a cell in a subject, inter alia, a patient, and the methods to facilitate the intracellular release and transfection of RNAi agents represent a treatment of the patient. In one embodiment, the patient suffers a disease, where the disease symptoms, the disease progression, or the disease outcome can be improved by alteration of protein expression in certain cell populations in the patient.

In certain embodiments, the cell is a cancer cell, where the treatment is a treatment that ameliorates the cancer in the patient. In one embodiment, a patient is afflicted with one or more of fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, Kaposi's sarcoma, acute promyeloid leukemia (APML), acute myelogenous leukemia (AML), chronic myelogenous leukemia (CML), acute lymphoblastic leukemia, chronic lymphocytic leukemia (CLL), prolymphocytic leukemia (PLL), hairy cell leukemia (HLL), Waldenstrom's macroglobulinemia (WM), non-Hodgkin's lymphoma, peripheral T-cell lymphomas, adult T-cell leukemia/lymphoma (ATL), cutaneous T-cell lymphoma (CTCL), large granular lymphocytic leukemia (LGF), erythroleukemias, lymphomas, Hodgkin's disease, embryonic carcinomas, or embryonic teratomas.

The following are some examples of uses of the methods and compositions. In a preferred embodiment, the said cell in the patient to be treated is a neoplastic cell in a pancreatic cancer that overexpresses hedgehog signaling, resulting in an enhanced growth rate of stromal cells in the tumor. A possible treatment of the patient comprises of administration of a siRNA directed against hedgehog signaling (inter alia, siRNA directed against expression of: sonic hedgehog, Gli family of transcription factors, or Smoothened), formulated in PCat liposomes as described in Example 1 of this application. The patient also would receive a small and sub-therapeutic dose of an enabler agent. The exemplary use of an enabler agent is discussed below. An example is the administration of paclitaxel, resulting in a concentration-time product of less than 1200 nM-hr, 600 nM-hr, 400 nM-hr, 240 nM-hr, 120 nM-hr, 60 nM-hr, or 40 nM-hr in the plasma of the patient, where a concentration-time product of 40 nM-hr requires a paclitaxel dose of approximately 20 µg/m$^2$ in a human patient. Less than four hours or preferably less than one hour after administration of paclitaxel, the RNAi formulation is administered. The dose of RNAi in the formulation is initially chosen as a low dose, e.g., 120 nmol/m$^2$ for a human patient, and is increased in subsequent patients according to standard methods in the art, depending on toxicity and activity.

Other enabler agents also may be used. An example is nocodazole. In one embodiment, the patient would receive a small and sub-therapeutic dose of nocodazol, resulting in a concentration-time product of less than 12000 nM-hr, 6000 nM-hr, 4000 nM-hr, 2400 nM-hr, 1200 nM-hr, 600 nM-hr or 400 nM-hr in the plasma of the patient. Less than four hours, and preferably less than one hour after administration of nocodazole, the RNAi formulation is administered. Other enablers could similarly be used at doses determined by the agent's potency and pharmacokinetics. For example, docetaxel, vincristine, or doxorubicin could be used at concentration-time products similar to paclitaxel, while colchicine could be used at a concentration-time product similar to nocodazole.

As another example, the said cell overexpresses oncogenic Ras (H-Ras, K-ras, or N-ras), resulting in enhanced tumor growth or chemoresistance in the tumor. A possible treatment of the patient comprises of administration of an siRNA directed against Ras signaling (Includes PI3K, AKT, MEK, or ERK), formulated in PCat liposomes as described in Example 1 of this application. The patient would receive a small and sub-therapeutic dose of an enabler agent, e.g., paclitaxel, as indicated above for the treatment against the hedgehog signaling.

In yet another example, the cell shows enhanced Wnt/β-catenin signaling, resulting in enhanced tumor growth or chemoresistance in the tumor. A possible treatment of the patient comprises of administration of an siRNA directed against β-catenin, formulated in PCat liposomes as described in Example 1 of this application. The patient would receive a small and sub-therapeutic dose of an enabler agent, e.g., inter alia, paclitaxel, as indicated above for the treatment against the hedgehog signaling.

In another embodiment, examples of diseases that can be managed by RNAi therapy are, inter alia, genetic disorders, metabolic disorders, and infectious diseases. In infectious diseases caused by RNA viruses, such as, inter alia, HIV-1, HIV-2, hepatitis A, hepatitis C, complementarity of the RNAi sequence to a section of the viral RNA results in cleavage of the viral RNA via RNA interference. Other infectious diseases, caused by nematodes and certain pathogenic protozoa, rely on RNA-mediated processes for recognition and invasion of target cells. These RNA-mediated processes can be targeted with RNAi therapy. More generally, infectious diseases caused by any type of pathogen, including viruses, bacteria, fungi, parasitic protozoa, nematodes, etc. can be treated with RNAi therapy. In genetic disorders and metabolic disorders, protein overexpression can be reversed with siRNA therapy. Examples of genetic and metabolic diseases that potentially can be treated with RNAi therapy are, inter alia, diseases of the eye such as age-related macular degeneration, diabetic retinopathy, diabetic macular edema, and glaucoma, diseases of the skin, such as pachyonychia congenita, or CNS disorders, such as neurodegenerative diseases, amyotrophic lateral sclerosis, Huntington's disease, and Parkinson's disease.

In certain embodiments, administration of the RNAi agent and the enabler agent is by systemic, local, or regional administration. In an embodiment, administration of these agents is by regional administration. In an embodiment, these agents are administered by direct local injection into a readily accessible organ or by direct regional injection adjacent to a readily accessible organ. Examples are, inter alia, intravitreal administration for treatment of disorders of the eye, intrasynovial administration for disorders of the joint, intramuscular injection in the urinary bladder to treat disorder of the bladder. Another example is intraperitoneal administration into the peritoneal cavity, as illustrated in Example 2.

In certain embodiments, the cell is in a mammal. The mammal is an animal, e.g., inter alia, a mouse, a rat, a rodent, a rabbit, a dog, a cat, a cow, a pig, a horse, a monkey. The mammal is a human.

In another embodiment, the patient to be treated is a patient that suffers from a pancreatic cancer or ovarian cancer, which has spread to the abdominal cavity. The formulations described above will be used for the treatment of tumors in the peritoneal cavity and in tissues adjoining the peritoneal cavity, ascites tumors or tumors metastasized into the abdominal cavity.

In one embodiment, these formulations are used to treat a tumor located in organs or regions that are readily accessible by direct administration, e.g., in one or more of tissues within or adjacent to the peritoneal cavity, bladder tissue, brain tissue, prostate tissue, or lung tissue.

In a preferred embodiment, the cell is a cancer cell derived from a pancreatic cancer, a breast cancer, a prostate cancer, a head and neck cancer, or an ovarian cancer.

In certain embodiments, the cell is a cell in a tissue culture. The method of the invention, which promotes RNAi transfection by applying low concentrations of an enabler agent, is a mild and convenient method.

The following examples show the disclosure has been practiced, but they should not be construed as limiting the disclosure. In this application, all percentages, proportions, and amounts are by weight, unless otherwise indicated.

EXAMPLES

The examples outlined below describe the studies conducted using the following general methodologies.

Five different RNAi were used. K-Ras siRNA (sc-35731) and ꓱ-catenin siRNA (sc-29209) were obtained from Santa Cruz Biotechnology. Survivin siRNA against wild type survivin was obtained from Cell Signaling Technology, Danvers, Mass. Non-target siRNA (siGENOME Non-targeting siRNA #1) and siGLO (D-001630) was obtained from Thermo Scientific Dharmacon. The non-target siRNA contains a random nucleotide sequence designed not to inhibit any known mRNA in human, mouse or rat genes.

Survivin and ꓱ-catenin are chemoresistance genes. K-ras is an oncogene. Knockdown of these molecules produces antitumor activity or enhances the activity of other forms of cytotoxic treatment such as chemotherapy. siGLO comprises a fluorescent 22 nucleotide RNA duplex that does not interfere or compete with functional siRNA. siGLO contains a nuclear transport peptide that causes siGLO in the cytoplasm to translocate to the nucleus (DharmaconProducts Technical Support, Http://Www.Dharmacon.Com/UploadedFiles/Home/Resources/Product Literature/Siglo-Green-Red-Tech-Note.Pdf; 2007; DharmaconProducts Technical Support, Http://Www.Sorvall.Com/EThermo/CMA/PDFs/Various/File_5514.Pdf, 2008).

The enabler agents include tubulin-active agents (including, inter alia, paclitaxel, docetaxel, cabazitaxel, colchicine, nocodazole, vincristine) and topoisomerase inhibitors (including, inter alia, doxorubicin).

Six cationic liposomes were used as vectors of RNAi. One formulation, comprising 50:50 (molar ratio) DOTAP:Cholesterol, was described in the art (inter alia, U.S. Pat. No. 6,413,544); this is referred to as DC liposomes. The second formulation, comprising DOTAP:Cholesterol:DOPE:DSPE-PEG2000 in a molar ratio of 50:30:19:1, is referred to as PCat liposomes. The third through the sixth formulations contain the same lipids in the same molar ratio as PCat liposomes plus a small amount of an enabler agent, i.e., paclitaxel, docetaxel, colchicine, or vincristine, and are denoted as Pac-PCat, Doc-PCat, Col-PCat, and Vin-PCat, respectively. The second through the sixth formulations are new and have not been described in the art.

RNAi agents are administered either as free (i.e., not incorporated into a lipid vector, denoted as free RNAi) or in lipid vectors. The latter is denoted as PCat-RNAi or DC-RNAi, in accordance to the lipid vectors used, i.e., PCat or DC liposomes.

In the cases where the enabler agent was administered separately from the RNAi agent, either in the form of pre-treatment or co-treatment, the enabler agent was dissolved in the culture medium in which the cells were incubated.

Transfection studies were performed in near-confluent cells (>80% confluence), when the efficiency of transfection is expected to the lowest. Confluence also more closely mimics the in vivo situation of cell growth, where cells grow in close proximity to each other.

In vivo antitumor activity was measured in tumor-bearing animals. In vitro antitumor activity was measured in cultured cells using the microtetrazolium assay (MTT). This assay measures the ability of cells to reduce the MTT dye, and is generally used as a measurement of the total cell number.

The effectiveness of RNAi therapy was measured by monitoring the level of the protein derived from the targeted gene mRNA using Western Blotting. For this purpose, the RNAi agent was siRNA against survivin, K-ras, or ꓱ-catenin.

The effectiveness of RIDES in enhancing the intracellular bioavailability of RNAi (i.e., promoting the delivery of RNAi to the cytosol and the release of RNAi from liposomes, endosomes or lysosomes) was studied by monitoring the intracellular trafficking and locations of lipid vectors and RNAi using confocal fluorescence microscopy. For this purpose, the RNAi agent was siGLO. siGLO shows green fluorescence. For monitoring the location of liposomes, rodamine-labeled lipids (red fluorescence) was added to the liposome during liposome preparation. Internalization of siGLO-containing liposomes into the cytosol of a cell yields punctuated red and green fluorescence signals. Co-localization of red and green signals indicates that siGLO is retained in the liposomes, whereas separation of red and green fluorescence signals indicate siGLO is released from liposomes. Similarly, appearance of green fluorescence in the nucleus indicates siGLO has been released from endosomes and liposome carriers; this is because only the free siGLO, with its nuclear transport peptide, can enter the nucleus.

Example 1

Preparation of Lipid Vectors of RNAi

The cationic liposomes were prepared as follows. The desired weight of each of the lipids is combined and dissolved in a mixture of chloroform and methanol in a 90:10 volume ratio. For preparation of Pac-PCat-RNAi, the required amount of paclitaxel is added to the dissolved lipids. Paclitaxel was added in weight ratios of 0.04-0.2% of the total weight of lipids, where a weight ratio of 0.04% provides a total equivalent paclitaxel concentration of 10 nM in medium in a typical in vitro experiment, and 0.2% provides a concentration of 50 nM. For Doc-PCat-RNAi, Col-PCat-RNAi and Vin-PCat-RNAi, docetaxel, colchicine and vincristine were added to provide a total equivalent medium concentration of 10 nM docetaxel, 100 nM colchicine, and 10 nM vincristine, respectively. For a typical total amount of lipids of 10 mg, a volume of 5 mL of chloroform/methanol is sufficient. The dissolved lipids are placed in a round bottom flask, and the organic phase is removed under a flow of nitrogen, resulting in a thin lipid layer on the internal glass surface of the flask. For 10 mg lipid, a round bottom flask with a volume of 10 mL can be used. The lipid layer is dried for an additional 12 hours under vacuum in a desiccator. The lipids are subsequently hydrated by adding RNase-free buffer (1 mL per 10 mg of total lipids), incubation at 60° C. for at least two hours, with gentle vortexing every 20 minutes, to form a liposomal suspension. The suspension is passed through a liposome extruder containing a filter, to reduce the liposome size to the preferred size, e.g., inter alia, using a 100 nm filter to obtain liposomes with a preferred diameter of about 100 nm.

For preparation of RNAi-loaded cationic liposomes, the prepared liposome suspension is gently mixed with RNAi stock solution (at concentrations of 2 µM to 10 µM) at room temperature. The RNAi amount is calculated to result in a charge ratio of RNAi to DOTAP of 1:4.

Example 2

Figure 1:
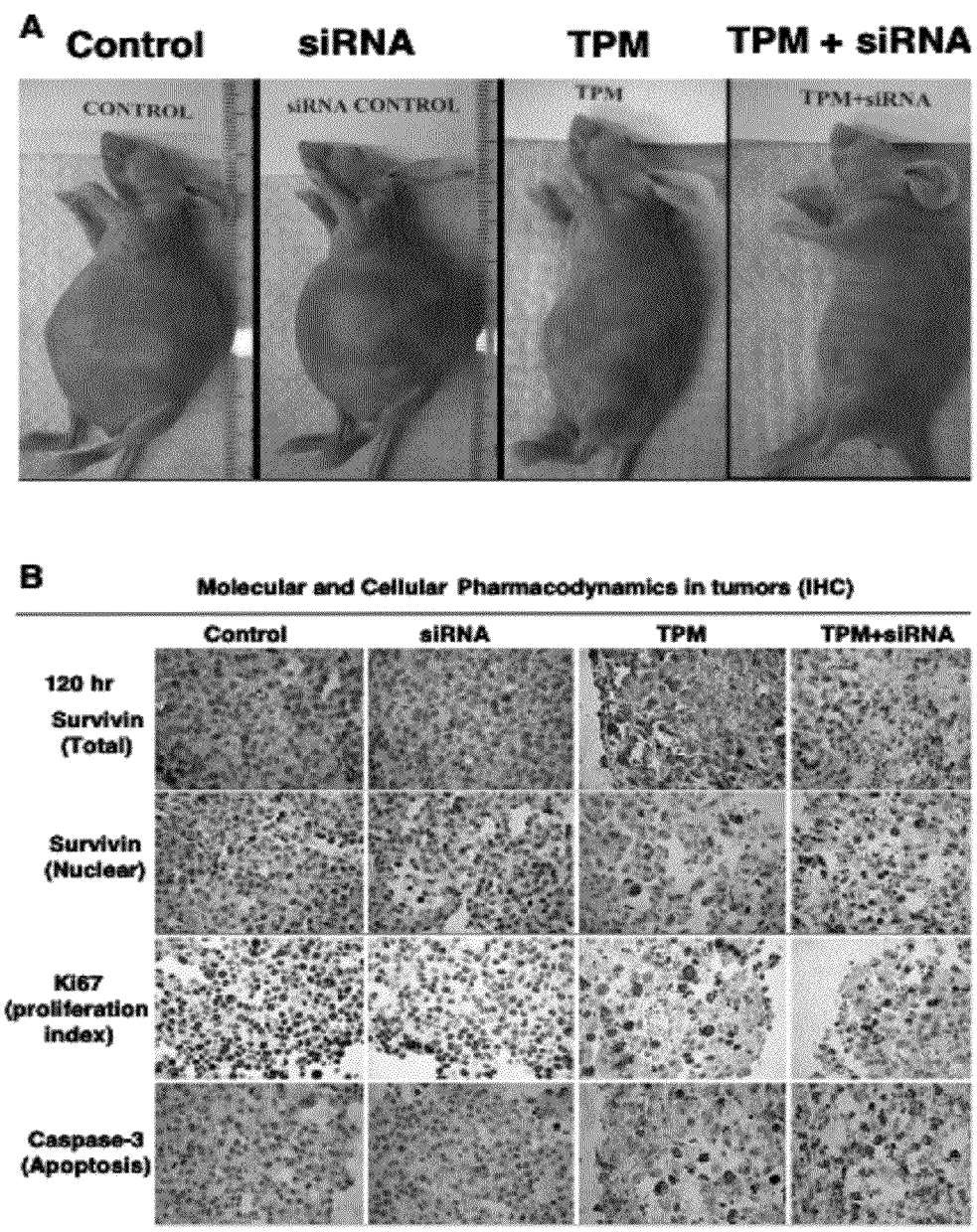
FIG. 1. RIDES with tumor priming is effective in vivo: Intraperitoneal treatment of peritoneal tumors.

RIDES Plus Tumor-Priming is Effective In Vivo: Intraperitoneal Treatment of Intraperitoneal Tumors The study was conducted in immunosuppressed mice carrying intraperitoneal Hs766T pancreatic cancer. Tumor cells were injected intraperitoneally into mice, which resulted in formations of tumors throughout the peritoneal cavity and eventual deaths in 100% of animals. Treatments were initiated 10 days after tumor implantation, or at approximately one-half of the expected survival time of untreated animals. All treatments were administered by intraperitoneal injections. Day 0 is the day of the first treatment and the survival time is the time from the first treatment. Paclitaxel was administered in the form of tumor-penetrating microparticles (TPM), prepared as described in U.S. patent application Ser. No. 11/242,546. Animals were given a single TPM dose (containing 80 mg/kg paclitaxel in rapid-release and slow-release particles). TPM, due to its rapid and slow release of paclitaxel, a drug that is both an apoptosis-inducing agent and an enabler agent, fulfill the dual functions of tumor-priming and promoting intracellular bioavailability of RNAi. The particle diameter of both formulations is approximately 4-6 µm. The RNAi was siRNA against survivin. The RNAi vector was PCat liposomes. PCat-RNAi was administered in two doses, at 72 hours and 120 hours after TPM administration, with each dose containing 1 nmole siRNA, and 0.12 mg DOTAP per animal. Animals were randomized according to tumor size into four treatment groups: RIDES plus tumor priming (TPM plus PCat-siRNA); TPM (TPM plus blank liposome carriers); siRNA (PCat-siRNA plus blank TPM particles); and Control (blank TPM particles plus blank PCat liposomes). Each treatment group comprised 21 to 25 animals. Median survival times and tumor-free cure rates (defined as absence of palpable tumor for >250 days after initiation of first treatment) are summarized in Table 1. The median survival time was 27 days for the two control groups that did not receive TPM (Control, siRNA), with a longer survival of 35 days for the TPM group, increasing to 62 days for the TPM+siRNA group. The TPM+PCat-siRNA group also showed an increased percentage of tumor-free cures. Photographs of animals in each of the treatment groups obtained on day 21 after tumor implantation are shown in FIG. 1A. These results indicate that RNAi alone had no antitumor activity, and that the addition of an enabler agent and an tumor priming (i.e., apoptosis-inducing) agent was necessary to obtain the therapeutic benefit from RNAi against survivin.

TABLE 1

Combination of enabler agent and apoptosis-inducing agent is required to obtain therapeutic benefits from RNAi against survivin: Intraperitoneal treatment of peritoneal tumors

| Group | n | Cure (%) | Median survival time (day) | Survival after treatment (day) | Increase in life span (%) |
|---|---|---|---|---|---|
| Control | 21 | 0.0 | 27 | 17 | 0 |
| siRNA | 21 | 0.0 | 27 | 17 | 0 |
| TPM | 25 | 8.0 | 35 | 25 | 47 |
| TPM + siRNA (RIDES plus tumor priming) | 24 | 25.0 | 62 | 52 | 205 |

In parallel experiments, tumors were harvested for each of the treatment groups at 96, 120, and 144 hour after TPM administration, and evaluated by immunohistochemistry for expression of total survivin (detected with polyclonal antibody), nuclear survivin (detected with a monoclonal antibody specific for wild type survivin), apoptosis (detected by caspase 3 expression and morphology), and inhibition of proliferation (detected by Ki-67 expression). Tumors from three animals were harvested per time point for each experimental group. Photomicrographs of representative specimens of the 120 hour time point are shown in FIG. 1B. Results of quantitative image analysis of the immunohistochemical staining intensity are shown in Table 2; these results indicate reduced expression of total and nuclear survivin, increased apoptosis, and decreased proliferation at all three time points for animals receiving TPM and PCat-siRNA (i.e., RIDES plus tumor priming), when compared to the group only received TPM. Single agent survivin siRNA did not reduce the baseline level of survivin in tumors and had no effects on tumor cell proliferation (measured as Ki67 labeling index) and apoptosis (caspase-3 labeling index). Consistent with the literature, TPM enhanced survivin expression in tumors, inhibited proliferation and produced apoptosis of tumor cells. Survivin siRNA down-regulated TPM-induced survivin expression, significantly enhanced TPM-induced antiproliferation and apoptosis, and extended the animal survival ($p<0.05$). These results indicate RIDES plus tumor priming, when the apoptosis-inducing agent and enabler agent were administered before RNAi, is effective in vivo.

Body weights of the animals in each of the treatment groups were determined over the course of the experiment. The time courses of body weights for the treatment groups receiving TPM with or without PCat-siRNA were similar, and did not show increased body weight loss for animals receiving TPM plus PCat-siRNA. All three treatment groups (single agent siRNA, TPM and their combination) produced <10% body weight loss, indicating no additional toxicity from PCat-siRNA.

To determine if the improved efficacy was due to changes in paclitaxel concentrations in tumor tissues, tumor tissues were analyzed using standard high performance liquid chromatographic methods. The results showed no difference in tissue paclitaxel concentrations for animals receiving RIDES plus tumor priming or TPM alone. This data indicates the improved efficacy was not due to increases in paclitaxel concentrations.

TABLE 2

Combination of enabler agent and apoptosis-inducing agent promote the delivery and expression of PCat-siRNA against survivin in vivo in intraperitoneal tumors

|  | 96 hr | 120 hr | 144 hr |
|---|---|---|---|
| Ki67 (%) | | | |
| Control | 76.5 | 76.5 | 76.5 |
| siRNA | 77.0 | 77.0 | 77.0 |
| TPM | 48.5 | 44.5 | 43.7 |
| TPM + siRNA (RIDES plus tumor priming) | 45.5 | 35.6 | 30.9 |
| Apoptosis (%) | | | |
| Control | 1.6 | 1.6 | 1.6 |
| siRNA | 1.4 | 1.4 | 1.4 |
| TPM | 20.1 | 19.1 | 15.5 |
| TPM + siRNA (RIDES plus tumor priming) | 25.2 | 33.9 | 28.9 |
| Survivin (detected by polyclonal antibody) (% of control) | | | |
| Control | 100 | 100 | 100 |
| siRNA | 114 | 114 | 114 |
| TPM | 228 | 959 | 433 |
| TPM + siRNA (RIDES plus tumor priming) | 166 | 268 | 216 |
| Survivin (detected by monoclonal antibody) (% of control) | | | |
| Control | 100 | 100 | 100 |
| siRNA | 117 | 117 | 117 |
| TPM | 92 | 64 | 42 |
| TPM + siRNA (RIDES plus tumor priming) | 46 | 40 | 22 |

Collectively, these data indicate that RIDES, comprising both the enabler agent paclitaxel and RNAi, together with tumor priming, (a) increases overall survival, (b) increases tumor-free cures, (c) reduces total survivin expression, (d) reduces nuclear survivin expression, (e) increases apoptosis, and (f) reduces tumor cell proliferation, compared to TPM or RNAi alone. These effects are not due to changes in paclitaxel accumulation in tumor tissue. These data indicate that RIDES plus tumor priming is effective in vivo when the enabler agent paclitaxel was administered before RNAi.

Example 3

RIDES is Effective In Vivo: Intravenous Treatments of Subcutaneous Tumors

This example shows that intravenous injection of RIDES is effective against systemic tumors. This study was performed in immunosuppressed mice carrying subcutaneously implanted human xenograft tumors. Three different tumor types were used, i.e., pancreatic Hs766T, prostate PC3, and pharynx FaDu. Treatments were initiated after tumors were established, defined as reaching a size of >3 mm. Paclitaxel was dissolved in 50:50 v/v Cremophor®:ethanol). The RNAi was siRNA against survivin. The RNAi vector was PCat liposomes, and contained 1 nmol siRNA against the wild-type survivin mRNA, and 0.12 mg DOTAP per animal. Day 0 is the day of the first treatment and the survival time is the time from the first treatment.

Figure 2:
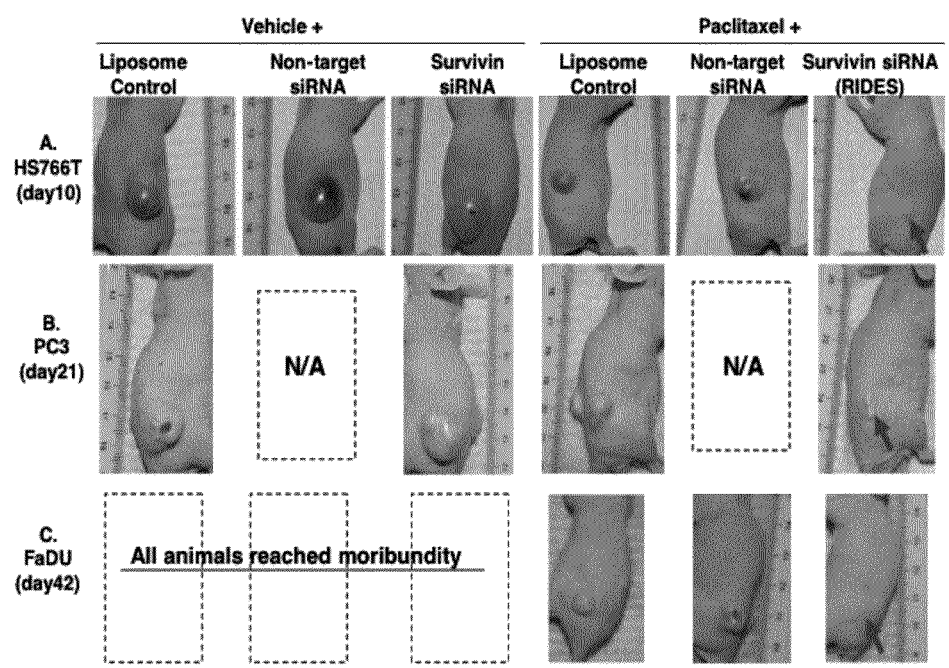
FIG. 2. RIDES is effective in vivo: Intravenous treatment of three different types of subcutaneous tumors.

Hs766T tumor-bearing mice were divided into six groups, randomized according to tumor size. Each treatment group consisted of 4 or 5 animals. Treatments were initiated when tumor size reached approximately 3 mm in diameter. At that time, animals received an intravenous injection of paclitaxel (20 mg/kg) or vehicle (50:50 v/v Cremophor®:ethanol), followed 3 days later by an intravenous injection of PCat liposomes containing survivin siRNA or non-target siRNA. A second dose of paclitaxel (20 mg/kg) or vehicle (Cremophor® and ethanol in 50:50 v/v) was administered 24 hours after RNAi treatment. The six treatment groups are: RIDES (paclitaxel plus PCat-RNAi against survivin), Pac+PCat-NT-RNAi (paclitaxel plus PCat-liposomes containing non-target siRNA), Pac+PCat (paclitaxel plus blank PCat liposomes), Vehicle+PCat-RNAi (vehicle plus PCat-siRNA against survivin), Vehicle+PCat-NT-RNAi (Vehicle plus PCat liposomes containing non-target siRNA), Vehicle+PCat (Vehicle plus blank PCat liposomes). FIG. 2A shows the tumor sizes at 10 days after the first treatment. The groups treated with vehicle, with or without PCat-NT-RNAi or PCat-RNAi, showed large tumors, indicating no therapeutic benefits from RNAi in the absence of paclitaxel. In comparison, the three groups that received paclitaxel, with or without PCat-NT-RNAi or PCat-RNAi showed smaller tumors, indicating paclitaxel produced some therapeutic benefits. A comparison of the Pac+PCat and Pac+PCat-NT-RNAi showed no difference, indicating no benefit from adding the non-target siRNA. In contrast, the RIDES group showed nearly invisible tumors, indicating synergy from combining paclitaxel and PCat-RNAi. Analysis of animal survival, tumor growth delay, and cures is provided in Table 3. Tumor growth rates were approximately equal in the three groups without paclitaxel administration and moribundity was reached for all animals between day 7 and day 17. Tumor growth was delayed in the groups that received only paclitaxel, with similar growth curves for the groups receiving blank PCat liposomes or PCat-NT-RNAi; the median survival in these latter two groups was 21 days. Tumor regression was observed only in the group treated with RIDES. This group also showed a prolonged survival, with a median of 28 days. One animal in this group (11%) showed complete tumor regression without recurrence for greater than 21 days.

Animals carrying PC3 tumors were treated similarly, with the exceptions of no PCat-NT-RNAi groups, that 4 doses of paclitaxel (10 mg/kg each) were administered on day 0, 4, 7, and 11, and 3 doses of PCat-RNAi administered on day 3, 6, and 10. FIG. 2B shows photographs of representative animals on day 21 after the first treatment. As in the mice carrying Hs766T, tumor regression was only observed in the group receiving RIDES. Survival and tumor growth analysis is presented in Table 3.

Animals carrying FaDu tumors were similarly treated as in animals carrying PC3 tumors, with the exceptions of a higher paclitaxel dose (20 mg/kg each) on days 0, 4, 8, and 12 and 2 doses of siRNA on days 3 and 11. FIG. 2C shows photographs of representative animals on day 42 after treatment initiation. As in the other tumor types, tumor regression was only observed in the group receiving RIDES. Survival and tumor growth analysis is presented in Table 3.

Together, these data indicate that intravenous RIDES, when both the enabler agent and PCat-RNAi against survivin were given intravenously, is effective in vivo and has broad activity against multiple types of tumors.

Cellular pharmacodynamics experiments were performed in satellite groups of mice implanted with the same 3 types of experimental tumors. Cell proliferation was measured by the Ki-67 index and apoptosis by the caspase 3 index. Treatment groups were as in the in vivo tumor growth/survival studies described above. For all tumor types, administration of paclitaxel (20 mg/kg) or vehicle was on days 0 and 4, and administration of siRNA (100 nM) or blank PCat liposomes was on day 3. Tumors were harvested on day 7 and processed for immunohistochemical analysis. Ki-67 and caspase 3 indices are the fraction of cells in a microscopic field showing positive antibody staining for the respective proteins. The cellular pharmacodynamics results are summarized in Table 4. In agreement with the survival and tumor growth data, the groups of animals that received only PCat-RNAi and PCat-NT-RNAi did not show significant decrease of proliferation or increase of apoptosis. In comparison, paclitaxel significantly decreased proliferation and increased apoptosis, which was further enhanced by adding PCat-RNAi against survivin.

TABLE 3

Enabler agent paclitaxel is required to obtain therapeutic benefits from RNAi: Systemic treatments of subcutaneous tumors in vivo.

|  | Vehicle + PCat | Vehicle + PCat-NT-RNAi | Vehicle + PCat-RNAi | Pac + PCat | Pac + PCat-NT-RNAi | RIDES |
|---|---|---|---|---|---|---|
| Hs766T | | | | | | |
| PFS, day | 4 | 4 | 4 | 7 | 10 | 25 |
| OS, day | 7 | 7 | 10 | 21 | 21 | 28 |
| TGD, day | 0 | 0 | 0 | 0 | 0 | 17* |
| Cure (%) | 0 | 0 | 0 | 0 | 0 | 11 |
| n | 3 | 3 | 3 | 9 | 5 | 9 |
| PC3 | | | | | | |
| PFS, day | 5.5 | Not included | 7 | 19 | Not included | 55.5 |
| OS, day | 21 | Not included | 17 | 38 | Not included | 75 |
| TGD, day | 0 | Not included | 0 | 17 | Not included | 31 |
| Cure (%) | 0 | Not included | 0 | 0 | Not included | 0 |
| n | 4 | Not included | 3 | 4 | Not included | 4 |
| FaDu | | | | | | |
| PFS, day | 3 | 3 | 3 | 21 | 24.5 | >98 |
| OS, day | 14 | 14.5 | 17.5 | 33 | 35 | >98 |
| TGD, day | 0 | 0 | 0 | 18 | 18 | 18* |
| Cure (%) | 0 | 0 | 0 | 17 | 0 | 67 |
| n | 5 | 4 | 4 | 6 | 4 | 6 |

Immunosuppressed mice were implanted subcutaneously with transplantable human pancreatic cancer (Hs766T), human prostate cancer (PC3), or human head and neck cancer (FaDu). Treatment with RIDES (paclitaxel plus PCat-siRNA against survivin) showed increased progression-free survival (PFS), overall survival (OS), and tumor growth delay (TGD), compared to the other five control/treatment groups. In animals implanted with Hs766T and FaDu tumors, the rate of cure (defined as no palpable tumor for >100 day after initiation of treatments) was increased. The PFS, OS and TGD values are median values N is number of animals.
*Completely regressed tumors (cures) are not included in TGD determination.

TABLE 4

Enabler agent paclitaxel is required to obtain therapeutic benefits from RNAi against survivin: Cellular pharmacodynamics.

|  | Vehicle + PCat | Vehicle + PCat-NT-RNAi | Vehicle + PCat-RNAi | Pac + PCat | Pac + PCat-NT-RNAi | RIDES |
|---|---|---|---|---|---|---|
| Hs766T | | | | | | |
| Ki-67 index, % | 73.8 | 73.8 | 75.1 | 47.8 | 52.3 | 31.7 |
| Caspase 3, % | 2.7 | 2.9 | 3.5 | 17.4 | 20.8 | 38.8 |
| PC3 | | | | | | |
| Ki-67 index, % | 40.4 | 36.4 | 34.5 | 28.4 | 28.7 | 12.0 |
| Caspase 3, % | 2.3 | 1.6 | 1.6 | 4.2 | 5.3 | 9.1 |

TABLE 4-continued

Enabler agent paclitaxel is required to obtain therapeutic benefits from RNAi against survivin: Cellular pharmacodynamics.

| | Vehicle + PCat | Vehicle + PCat-NT-RNAi | Vehicle + PCat-RNAi | Pac + PCat | Pac + PCat-NT-RNAi | RIDES |
|---|---|---|---|---|---|---|
| | | | FaDu | | | |
| Ki-67 index, % | 90.6 | Not included | 84.2 | 78.1 | Not included | 61.6 |
| Caspase 3, % | 5.2 | Not included | 2.3 | 14.2 | Not included | 17.7 |

Immunosuppressed mice were implanted subcutaneously with transplantable human pancreatic cancer (Hs766T), human prostate cancer (PC3), or human head and neck cancer (FaDu). Treatment with the combination of paclitaxel with an siRNA formulated in the PCat liposomes of Example 2 resulted in increases in anti-proliferation (determined by Ki-67 index) and apoptosis (determined by caspase 3 index).

Example 4

PCat-RNAi is More Effective In Vivo Compared to the Standard DC-RNAi

Mice carrying intraperitoneal Hs766T pancreatic cancer were used to compare the ability of two types of liposome RNAi carriers, i.e., PCat and DC liposomes, to enhance the antitumor activity of paclitaxel. The remaining methods were the same as described in Example 2. The results of survival analysis, shown in Table 5, indicate the greater in vivo efficacy of PCat-RNAi compared to DC-RNAi. Increase in life span is calculated as (Median survival time or MST in the experimental group minus MST of control) divided by (MST of control).

TABLE 5

| Group | n | Cure (%) | Median survival time after initiation of treatment* (day) | Increase in life span (%) |
|---|---|---|---|---|
| Control | 4 | 0 | 22.5 | 0 |
| DC-RNAi | 4 | 0 | 16.5 | −26 |
| PCat-RNAi | 4 | 0 | 20 | −11 |
| TPM | 4 | 20 | 44.5 | 98 |
| TPM + DC-RNAi | 5 | 40 | 59.0 | 162 |
| TPM + PCat-RNAi | 5 | 40 | 76.0 | 238 |

*Treatments were initiated on day 10 after tumor implantation

Example 5

PCat Liposomes are Less Toxic to Cultured Cells Compared to DC Liposomes

A known limitation of DOTAP-containing liposomes is its induction of cytotoxicity. This example compared the cytotoxicity of the standard liposome formulation in the art, i.e., DC liposomes, to the cytotoxicity of the PCat liposomes. Both formulations were prepared as described in Example 1. Cells in monolayer culture were exposed to varying DOTAP concentrations of either liposome (at concentrations of 0.1, 1, 2, 5, 10, 15, 50, 100, and 200 μg/ml). Cytotoxicity was determined in human ovarian cancer SKOV3 cells, human breast cancer MCF7 cells, and human prostate cancer PC3 cells. The results indicate greater than 50% loss of cell viability for the DC liposomes at a DOTAP concentration of 10 μg/ml. At this same concentration, the PCat liposomes did not cause loss of cell viability. A comparison of the concentration-effect curves at all DOTAP concentrations indicates that the PCat liposomes are at least 10-fold less cytotoxic compared to the DC liposomes.

Example 6

PCat Liposomes have Less Toxicity in Mice Compared to the DC Liposomes

This example compared the toxicity of the DC and PCat liposomes, in two studies. The first study evaluated the effect of blank liposomes (i.e., no RNAi) on the changes in animal body weights. Loss of body weight is a widely used general indicator of toxicity. Animals received, by intraperitoneal injection, varying doses of blank PCat or DC liposomes. The amount of liposomes administered was expressed in DOTAP equivalents, in doses of 0 mg/kg (saline control), 10, 50, and 100 mg/kg. Four or five animals were treated per group. The results show no significant body weight loss in the groups of animals that received PCat liposomes, while a statistically significant loss of approximately 3% of body weight was observed in animals receiving the highest dose of DC liposomes. These results indicate the greater safety of the PCat liposomes in vivo compared to the standard DC liposomes described in the art.

The second study evaluated the toxicity in mice receiving PCat or DC liposomes containing RNAi. The RNAi was siRNA against survivin. The two preparations were injected intravenously to tumor-free CD1 mice, and were evaluated for toxicity to the liver and spleen, organs of the reticuloendothelial system. Mice in groups of five animals each received formulations containing 1 nmole survivin siRNA and 0.12 mg DOTAP per animal, euthanized on day 7, and blood samples taken. The liver function analysis was by measurement of alanine aminotransferase (ALT) and aspartate aminotransferase (AST) levels. The spleens were harvested and weighed. Compared to control animals, the ALT, AST, and spleen weights of animals receiving the DC-RNAi were significantly increased (220%, 201%, and 126% of control, respectively, p<0.05). In contrast, no significant changes were observed in animals receiving PCat-RNAi (113%, 92%, and 108% of control, respectively, p>0.1). These data indicate PCat-RNAi has less host toxicity compared to DC-RNAi.

Example 7

Enabler Agent Enhances the Intracellular Bioavailability of RNAi

This example shows that enabler agents improve the delivery or release of RNAi molecules from their liposome carriers, endosomes, or lysosomes. Three studies were conducted using siGLO as the RNAi. The lipid vector was the DC liposomes. The study was performed in one or more of three human tumor cell lines, i.e., pancreatic Hs766T, breast cancer MCF7, and prostate cancer PC3.

The first study evaluated the effects of pretreatment with enabler agents. Hs766T, MCF7 and PC3 cells were treated with an enabler agent, including tubulin stabilizing agents (i.e., paclitaxel, docetaxel), tubulin depolymerizing agents (i.e., vincristine, colchicine, nocodazole), and a topoisomerase inhibitor (doxorubicin). Additional cytotoxic agents not acting through tubulin interaction or topoisomerase inhibition, i.e., cisplatin and 5-fluorouracil, were included as side-by-side comparisons. Cells were treated with one of these agents for 4 hours, followed by incubation with liposomal siGLO for 6 hours. Control cells had no drug treatments. After pretreatment with enabler agent, cells were washed with cold FBS-free medium for 3 times, fixed with formalin, stained with the nucleus dye DRAQ5, and examined using confocal fluorescence microscopy. The results, presented in FIG. 3, show that in control cells, most of the red fluorescence (lipids) co-localized with the green fluorescence (siGLO), indicating that DC-RNAi entered in cells primarily as intact lipoplexes. Both red and green fluorescence signals were punctated and located in the cytoplasm or the perinuclear regions, indicating little siGLO was released into the cytosol. Pre-treatment with an enabler agent induced nuclear accumulation of green fluorescence signals, as indicated by the co-localization of the green signal with the blue nucleus dye. Because only the free siGLO (not embedded in liposomes) can enter the nucleus, the nuclear accumulation of siGLO indicates the release of RNAi from the liposomes, endosomes, or lysosomes. These observations were common to all three tested cell lines. In contrast, pretreatment with other cytotoxic agents, i.e. cisplatin or 5-fluorouracil, did not change the punctated pattern of siGLO localization. These results indicate tubulin-active agents and topoisomerase inhibitors selectively enable the release of RNAi from liposomes, endosomes or lysosomes.

The second study evaluated the concentration-dependence of the paclitaxel effect on RNAi transfection. HS766T cells were treated with paclitaxel at concentrations of 10 and 50 nM for 4 hours. The treatment with 10 nM paclitaxel for 4 hours, as indicated by the measurement of cytotoxicity using the MTT assay, had no apparent toxicity, compared to control cells without drug treatment. In contrast, the treatment with 50 nM for 4 hours induced 10 to 30% cytotoxicity. The results, shown in FIG. 4A, indicate enhanced the appearance of siGLO in the nucleus at both concentrations. This result shows that a tubulin-active agent, at a wide range of concentrations and treatment durations that are cytotoxic and sub-cytotoxic, can improve the delivery and release of RNAi to the cytosol. This is surprising as one might anticipate that overt cytotoxicity would impede cellular processes, including cellular processes involving tubulin/microtubule functions and RNAi machinery.

The above two studies indicate that pretreatment with an enabler agent that preceded siGLO treatment by four hours enhanced the RNAi. The third study showed that concurrent treatments with an enabler agent also produced the same benefit. Conditions were as described above, except that treatment with the tubulin-active agents paclitaxel and nocodazole, and the cytotoxic agents cisplatin, were concurrent with the siGLO treatment. The study was performed in prostate cancer PC3 cells. Analysis by confocal microscopy of the treated cells showed extensive nuclear accumulation of siGLO for cells receiving the tubulin-active agents, but not for control cells and cells treated with cisplatin (FIG. 4B). These side-by-side comparisons indicate pretreatment or concurrent treatment with an enabler agent enhances the release of RNAi from liposomes, endosomes or lysosomes, or liposomes, and improves the RNAi delivery to the cytosol and nucleus.

Example 8

The Paclitaxel Concentrations Required to Enhance the Intracellular Bioavailability of RNAi can be Readily Accomplished at Non-Cytotoxic Concentrations in Normal Cells This example shows that the paclitaxel concentrations that enable the delivery and release of RNAi to the cytosol do not cause toxicity in normal cells. This was evaluated in porcine arterial smooth muscle cells; the duration of drug treatment was 36 hours. The cytotoxicity of paclitaxel in cancer cell lines was evaluated in pancreatic HS766T, prostate PC3 and breast MCF7 cells; the treatment duration was 48 hours. Cytotoxicity was measured using the using the MTT assay. The data, summarized in Table 6, show the 50%-inhibitory paclitaxel concentrations in different cell lines. In order to compare the relative effects of paclitaxel in tumor and smooth muscle cells that were treated for different time durations, the concentration time product or C×T was calculated. For smooth muscle cells, the paclitaxel C×T that produced 50% cytotoxicity was 4068 nM×hr, or 6- to 16-times higher compared to the paclitaxel C×T that produced 50% cytotoxicity in HS766T, MCF7, and PC3 cancer cells. This data indicates that the paclitaxel concentrations required to enhance the transfection of RNAi can be readily accomplished at non-cytotoxic concentrations in normal cells.

TABLE 6

| Cell Lines | Smooth Muscle Cells | HS766T | MCF7 | PC3 |
|---|---|---|---|---|
| 50% inhibition of IC50 (nM) | 113 | 12.7 | 5.2 | 15.5 |
| C×T (nM×hr) | 4068 | 610 | 250 | 744 |

Example 9

RIDES Against Survivin or K-Ras Enhanced the Antitumor Activity of Paclitaxel

This example used five cell lines, i.e., human pancreatic Hs766T, human pancreatic MiaPaCa-2, human breast MCF7, human prostate PC3, and human head and neck FaDu. Cells were cultured in monolayer and used when the cultures were over 80% confluent. Cells then were treated with paclitaxel, followed by treatment with either PCat-siRNA against survivin (100 nM) or against K-ras (100 nM). The control groups were single agent paclitaxel, single agent PCat-siRNA, paclitaxel plus non-target siRNA, or no treatments. In all five cell lines, RIDES (paclitaxel plus PCat-siRNA) against either survivin or K-ras yielded significantly greater antitumor activity compared to single agents.

Example 10

RIDES is Effective in Knocking Down Target Proteins in the Presence of Paclitaxel The effectiveness of PCat-siRNA against survivin, β-catenin, and K-ras in knocking down the protein level in the presence of paclitaxel was investigated in monolayer cultures of human prostate PC3, ovarian SKOV, head and neck FaDu, or pancreatic MiaPaCa-2 cells. Monolayer cells were treated with 10 nM paclitaxel for 4 hour, followed by a 4-6 hour treatment with PCat-RNAi (100 nM). At 48 hours after siRNA transfection, cells were harvested by scraping in ice-cold TBS and stored at −80° C. until analysis by Western Blot. Cellular proteins were extracted with a buffer extraction system and protein concentrations were determined using BCA reagents. For Western Blotting, equal amount of total proteins of each sample is separated on a SDS-PAGE and transferred to a PVDF membrane. The blots were probed using mouse monoclonal antibodies for survivin, β-catenin, or K-ras and housekeeping proteins for standardization. Visualization was by chemoluminescence. Treatment groups are as follows. The control group received paclitaxel and blank liposomes. The Pac+NT-siRNA groups received paclitaxel and non-target siRNA. The RIDES groups received paclitaxel and PCat-RNAi containing siRNA against survivin, β-catenin, or K-ras.

The results, presented in FIG. 5, show that PCat-RNAi, in the presence of paclitaxel, significantly suppressed survivin, β-catenin, or K-ras protein level. This indicates the effectiveness of RIDES.

Example 11

Various Composition of RIDES, Including Loading the Enabler Agent with RNAi into the Same PCat Liposomes, Improve the Intracellular Bioavailability of RNAi The above examples (i.e., Examples 2, 3, 7 and 10) show that RIDES is effective when the enabler agent is given as pretreatment or as concurrent treatment with PCat-RNAi, when the two components were given as separate entities. This example shows the effectiveness of RIDES to deliver and release RNAi to the cytosol, when the enabler agent and RNAi are both loaded in PCat liposomes and given as a single entity. The four enabler agents were paclitaxel, docetaxel, colchicine, and vincristine, and the corresponding respective entities are Pac-PCat-RNAi, Doc-PCat-RNAi, Col-PCat-RNAi, and Vin-PCat-RNAi. The study was performed in one or more of three human tumor cells, i.e., pancreatic Hs766T, breast MCF7, and prostate PC3. The PCat-RNAi contained a concentration of 50 nM siRNA in the cell culture medium. The studies used confocal fluorescence microscopy to examine the delivery of RNAi in cellular organelles. The RNAi was siGLO. Two studies were performed.

The first study compared three different ways to combine the two components of RIDES. Paclitaxel was used as the enabler agent in side-by-side comparison. Paclitaxel was administered as pretreatment or concurrent treatment with RNAi as described in Examples 7 and 10. The two agents also were administered in a single entity as Pac-PCat-RNAi. The paclitaxel-equivalent concentration in Pac-PCat-RNAi and in the culture medium was 10 nM. The results in PC3 cells, presented in FIG. 6A, show the presence of siGLO in the nucleus, indicating Pac-PCat-RNAi is effective in enhancing the intracellular bioavailability of RNAi.

The second study showed similar beneficial effects for Doc-PCat-RNAi, Col-PCat-RNAi, and Vin-PCat-RNAi, in three human cancer cell lines, i.e., prostate PC3, breast MCF7 and pancreatic Hs766T. These preparations contained the drug-equivalent concentration of 10 nM docetaxel, 100 nM colchicine, and 10 nM vincristine. The results, presented in FIG. 6B, show higher intensity of siGLO in the nucleus of cells treated with enabler-loaded PCat-RNAi compared to PCat-RNAi without the enabler-loading, in all three cell lines.

In summary, the above results indicate that enabler agent-loaded PCat-RNAi is effective to deliver the RNAi agent to the cytosol and to promote the release of the RNAi agent from liposomes, endosomes, and lysosomes.

Example 12

Various Compositions of RIDES, Including Loading the Enabler Agent with RNAi into the Same PCat Liposomes, Improve the Effectiveness of RNA Interference This example shows that various compositions of RIDES produce effective RNA interference. The experiments used human pancreatic HS766T cells. The RNAi was siRNA against survivin. The control group had no treatment. Some groups used nontarget RNAi (NT-RNAi) instead of siRNA against survivin.

In the first study, cells were treated for 6 hours with Pac-PCat-RNAi, or with the two components, i.e., paclitaxel and PCat-RNAi given concurrently as two separate entities. Cells were harvested at 72 hours after initiation of siRNA treatment and analyzed for the survivin protein levels using Western Blotting. The blots were probed using mouse monoclonal antibodies for survivin and the housekeeping protein actin (for standardization). The results, presented in FIG. 7A, indicate that separately-administered paclitaxel and PCat-RNAi yielded partial knockdown or survivin, whereas Pac-PCat-RNAi yielded nearly complete protein knockdown.

The second study used Doc-PCat-RNAi, Col-PCat-RNAi, and Vin-PCat-RNAi. The results, presented in FIG. 7B, show that all three preparations yielded survivin protein knockdown.

EQUIVALENTS

Those skilled in the art will recognize, or be able to ascertain, using no more than routine experimentation, many equivalents to specific embodiments of the disclosure described specifically herein. Such equivalents are encompassed in the scope of the following claims.

While the methods and compositions have been described with reference to various embodiments, those skilled in the art will understand that various changes may be made and equivalents may be substituted for elements thereof without departing from the scope and essence of the disclosure. Additionally, many modifications may be made to adapt a particular situation or material to the teachings of the disclosure without departing from the essential scope thereof. Therefore, it is intended that the disclosure may not be limited to the particular embodiments disclosed, but that the disclosure will include all embodiments falling within the scope of the appended claims. In this application the US measurement system is used, unless otherwise expressly indicated. Also, all citations referred to herein are expressly incorporated herein by reference.

REFERENCES

Patent References

WO/2006/099445
U.S. Pat. No. 5,459,127

Non-Patent References

CABANES, A, BRIGGS, K E, GOKHALE, P C et al., Comparative in vivo studies with paclitaxel and liposome-encapsulated paclitaxel. *Int. J. Oncol.*, yr 1998, pp. 1035-1040, vol. 12.

CARTHEW, R W, and SONTHEIMER, E J, Origins and Mechanisms of miRNAs and siRNAs. *Cell*, yr 2009, pp. 642-655, vol. 136.

DENIZOT, F, and LANG, R, Rapid colorimetric assay for cell growth and survival. Modifications to the tetrazolium dye procedure giving improved sensitivity and reliability. *J. Immunol. Methods*, yr 1986, pp. 271-277, vol. 89.

DHARMACONPRODUCTS TECHNICAL SUPPORT. Transfection optimization using siGLO Green and siGLO Red transfection indicators. Http://Www.Dharmacon.Com/UploadedFiles/Home/Resources/Product_Literature/Siglo-Green-Red-Tech-Note.Pdf. 2007. Thermo Fisher Scientific Inc.

DHARMACONPRODUCTS TECHNICAL SUPPORT. Thermo Scientific Dharmacon® siGLO® transfection indicators. Http://Www.Sorvall.Com/EThermo/CMA/PDFs/Various/File_5514. Pdf. 2008.

DUZGUNES, N, GOLDSTEIN, J A, FRIEND, D S et al., Fusion of liposomes containing a novel cationic lipid, N-[2,3-(dioleyloxy)propyl]-N,N,N-trimethylammonium: induction by multivalent anions and asymmetric fusion with acidic phospholipid vesicles. *Biochemistry*, yr 1989, pp. 9179-9184, vol. 28.

FELGNER, P L, GADEK, T R, HOLM, M et al., Lipofection: a highly efficient, lipid-mediated DNA-transfection procedure. *Proc. Natl. Acad. Sci. U.S.A*, yr 1987, pp. 7413-7417, vol. 84.

GHILDIYAL, M, and ZAMORE, P D, Small silencing RNAs: an expanding universe. *Nat. Rev. Genet.*, yr 2009, pp. 94-108, vol. 10.

GONDI, C S, and RAO, J S, Concepts in in vivo siRNA delivery for cancer therapy. *J. Cell Physiol*, yr 2009, pp. 285-291, vol. 220.

GRIMM, D, Small silencing RNAs: state-of-the-art. *Adv. Drug Deliv. Rev.*, yr 2009, pp. 672-703, vol. 61.

HASEGAWA, S, HIRASHIMA, N, and NAKANISHI, M, Microtubule involvement in the intracellular dynamics for gene transfection mediated by cationic liposomes. *Gene Ther.*, yr 2001, pp. 1669-1673, vol. 8.

ILLUM, L, and DAVIS, S S, The organ uptake of intravenously administered colloidal particles can be altered using a non-ionic surfactant (Poloxamer 338). *FEBS Lett.*, yr 1984, pp. 79-82, vol. 167.

ILLUM, S L, and DAVIS, S S, Effect of the nonionic surfactant poloxamer 338 on the fate and deposition of polystyrene microspheres following intravenous administration. *J. Pharm. Sci*, yr 1983, pp. 1086-1089, vol. 72.

INOUE, M, MATSUMOTO, S, SAITO, H et al., Intraperitoneal administration of a small interfering RNA targeting nuclear factor-kappa B with paclitaxel successfully prolongs the survival of xenograft model mice with peritoneal metastasis of gastric cancer. *Int. J. Cancer*, yr 2008, pp. 2696-2701, vol. 123.

JINEK, M, and DOUDNA, J A, A three-dimensional view of the molecular machinery of RNA interference. *Nature*, yr 2009, pp. 405-412, vol. 457.

KLIBANOV, A L, MARUYAMA, K, BECKERLEG, A M et al., Activity of amphipathic poly(ethylene glycol) 5000 to prolong the circulation time of liposomes depends on the liposome size and is unfavorable for immunoliposome binding to target. *Biochim. Biophys. Acta*, yr 1991, pp. 142-148, vol. 1062.

KOUDELKA, S, TURANEK-KNOTIGOVA, P, MASEK, J et al., Liposomes with high encapsulation capacity for paclitaxel: Preparation, characterisation and in vivo anticancer effect. *J. Pharm. Sci.*, yr 2010, pp. 2309-2319, vol. 99.

LANDEN, C N, JR., CHAVEZ-REYES, A, BUCANA, C et al., Therapeutic EphA2 gene targeting in vivo using neutral liposomal small interfering RNA delivery. *Cancer Res.*, yr 2005a, pp. 6910-6918, vol. 65.

LANDEN, C N, JR., CHAVEZ-REYES, A, BUCANA, C et al., Therapeutic EphA2 gene targeting in vivo using neutral liposomal small interfering RNA delivery. *Cancer Res.*, yr 2005b, pp. 6910-6918, vol. 65.

LITZINGER, D C, BUITING, A M, VAN ROOIJEN, N et al., Effect of liposome size on the circulation time and intraorgan distribution of amphipathic poly(ethylene glycol)-containing liposomes. *Biochim. Biophys. Acta*, yr 1994, pp. 99-107, vol. 1190.

MOGHIMI, S M, and DAVIS, S S, Innovations in avoiding particle clearance from blood by Kupffer cells: cause for reflection. *Crit Rev. Ther. Drug Carrier Syst.*, yr 1994, pp. 31-59, vol. 11.

MOGHIMI, S M, and PATEL, H M, Serum factors that regulate phagocytosis of liposomes by Kupffer cells. *Biochem. Soc Trans*, yr 1993, pp. 128S, vol. 21.

MORRISSEY, D V, LOCKRIDGE, J A, SHAW, L et al., Potent and persistent in vivo anti-HBV activity of chemically modified siRNAs. *Nat. Biotechnol.*, yr 2005, pp. 1002-1007, vol. 23.

NAIR, R R, RODGERS, J R, and SCHWARZ, L A, Enhancement of transgene expression by combining glucocorticoids and anti-mitotic agents during transient transfection using DNA-cationic liposomes. *Mol. Ther.*, yr 2002, pp. 455-462, vol. 5.

NIELSEN, L L, LIPARI, P, DELL, J et al., Adenovirus-mediated p53 gene therapy and paclitaxel have synergistic efficacy in models of human head and neck, ovarian, prostate, and breast cancer. *Clin. Cancer Res.*, yr 1998, pp. 835-846, vol. 4.

NOF CORPORATION. PEGylated lipids. Http://Www.Phospholipid.Jp/Phospholipid_2-3.Html. 2010.

NORMAN, M E, WILLIAMS, P, and ILLUM, L, Influence of block copolymers on the adsorption of plasma proteins to microspheres. *BIOMATERIALS*, yr 1993, pp. 193-202, vol. 14.

SANTEL, A, ALEKU, M, KEIL, O et al., A novel siRNA-lipoplex technology for RNA interference in the mouse vascular endothelium. *Gene Ther.*, yr 2006, pp. 1222-1234, vol. 13.

SIRNA THERAPEUTICS INC. Partnering opportunities. Http://Www.Sirna.Com. 2009.

SOUTSCHEK, J, AKINC, A, BRAMLAGE, B et al., Therapeutic silencing of an endogenous gene by systemic administration of modified siRNAs. *Nature*, yr 2004, pp. 173-178, vol. 432.

WU, S Y, and MCMILLAN, N A, Lipidic systems for in vivo siRNA delivery. *AAPS. J.*, yr 2009, pp. 639-652, vol. 11.

YANG, T, CUI, F D, CHOI, M K et al., Enhanced solubility and stability of PEGylated liposomal paclitaxel: in vitro and in vivo evaluation. *Int. J. Pharm.*, yr 2007, pp. 317-326, vol. 338.

We claim:

1. An RNAi Delivery and Expression System (RIDES) composition comprising:

(a) a liposomal formulation, where the lipid component comprises DOTAP, Cholesterol, DOPE, and DSPE-PEG2000 in a molar ratio of about 50:30:19:1, wherein the charge ratio between RNAi agent and DOTAP is between 1:1 and 1:10, wherein the liposomal formulation further contains one or more enabler agents selected from the group consisting of paclitaxel, docetaxel, vincristine, colchicine, nocodazole, and doxorubicin, plus an RNA interference (RNAi) agent selected from the group consisting of small interfering RNA (siRNA), double-stranded RNA (dsRNA), single-stranded RNA (ssRNA), micro-RNA (miRNA), and short hairpin RNA (shRNA); and (b) a pharmaceutically acceptable carrier.

2. The RIDES composition of claim 1, wherein said RNAi agent inhibits the translation of a gene that promotes growth of a hyperplastic or cancerous mammalian cell.

3. The RIDES composition of claim 2, wherein said gene is survivin, K-ras, or β-catenin.

4. The RIDES composition of claim 1, wherein said RNAi agent inhibits the translation of a gene involved in a non-cancerous disorder.

5. The RIDES composition of claim 1, wherein said one or more enabler agents are present at a subtherapeutic dose.

6. The RIDES composition of claim 5, wherein said one or more enabler agents comprises paclitaxel and the paclitaxel dose produces a concentration-time product of about 40 nM-hr.

7. A composition comprising:

(a) a liposomal formulation, where the lipid component comprises DOTAP, Cholesterol, DOPE, and DSPE-PEG2000 in a molar ratio of about 50:30:19:1, an RNAi agent, wherein the charge ratio between RNAi agent and DOTAP is between 1:1 and 1:10; and wherein the liposomal formulation further contains one or more enabler agents, selected from the group consisting of paclitaxel, docetaxel, vincristine, colchicine, nocodazole and doxorubicin; and (b) a pharmaceutically acceptable carrier.

8. A method for delivering an RNAi agent to a cell cultured in vitro, comprising contacting said cell with the RIDES composition of claim 1.

9. A method for delivering an RNAi agent to a cell in a subject, comprising contacting said cell with the RIDES composition of claim 1.

10. The method of claim 9, wherein said cell is a hyperplastic cell or a tumor cell in a patient.

11. The method of claim 10, wherein said hyperplastic cell or tumor cell is a cell in one or more of a pancreatic cancer, a breast cancer, a prostate cancer, a head and neck cancer, or an ovarian cancer.

12. A method for delivering an RNAi agent to a cell cultured in vitro, comprising contacting said cell with the liposomal RNAi composition of claim 7.

13. A method for delivering an RNAi agent to a cell in a subject, comprising contacting said cell with the liposomal RNAi composition of claim 7.

14. The method of claim 13, wherein said cell is a hyperplastic cell or a tumor cell in a patient.

15. The liposomal RNAi composition of claim 7, wherein said RNAi agent inhibits the translation of a gene that promotes growth of a hyperplastic or cancerous mammalian cell.

16. The liposomal RNAi composition of claim 15, wherein said gene is survivin, K-ras, or β-catenin.

17. The liposomal RNAi composition of claim 7, wherein said RNAi agent inhibits the translation of a gene involved in a non-cancerous disorder.

18. The liposomal RNAi composition of claim 7, wherein said one or more enabler agents are present at a subtherapeutic dose.

19. The liposomal RNAi composition of claim 18, wherein said one or more enabler agents comprises paclitaxel and the paclitaxel dose produces a concentration-time product of about 40 nM-hr.

20. The method of claim 14, wherein said hyperplastic cell or tumor cell is a cell in one or more of a pancreatic cancer, a breast cancer, a prostate cancer, a head and neck cancer, or an ovarian cancer.

* * * * *

UNITED STATES PATENT AND TRADEMARK OFFICE
CERTIFICATE OF CORRECTION

PATENT NO. : 8,802,138 B2
APPLICATION NO. : 13/444798
DATED : August 12, 2014
INVENTOR(S) : Jessie L.-S. Au et al.

Page 1 of 1

It is certified that error appears in the above-identified patent and that said Letters Patent is hereby corrected as shown below:

In the Claims
Col. 43 line 34, insert --and-- before "wherein";
  lines 35-39, delete ", and wherein the liposomal formulation further contains one or more enabler agents, selected from the group consisting of paclitaxel, docetaxel, vincristine, colchicine, nocodazole and doxorubicin"

Signed and Sealed this
Thirtieth Day of December, 2014

Michelle K. Lee
*Deputy Director of the United States Patent and Trademark Office*